US00RE48801E

(19) United States
(12) Reissued Patent
Marine et al.

(10) Patent Number: US RE48,801 E
(45) Date of Reissued Patent: Nov. 2, 2021

(54) INHIBITION OF A LNCRNA FOR TREATMENT OF MELANOMA

(71) Applicants: VIB VZW, Ghent (BE); KATHOLIEKE UNIVERSITEIT LEUVEN, K.U.LEUVEN R&D, Leuven (BE); UNIVERSITEIT GENT, Ghent (BE)

(72) Inventors: Jean-Christophe Marine, Linden (BE); Eleonora Leucci, Linden (BE); Joke Vandesompele, Zulte (BE); Pieter Mestdagh, Bruges (BE)

(73) Assignees: VIB VZW, Ghent (BE); Katholieke Universiteit Leuven, K.U. Leuven R&D, Leuven (BE); Universiteit Gent, Ghent (BE)

(21) Appl. No.: 16/689,648

(22) Filed: Nov. 20, 2019

Related U.S. Patent Documents

Reissue of:
(64) Patent No.: 9,821,004
Issued: Nov. 21, 2017
Appl. No.: 14/913,629
PCT Filed: Aug. 20, 2014
PCT No.: PCT/EP2014/067781
§ 371 (c)(1),
(2) Date: Feb. 22, 2016
PCT Pub. No.: WO2015/024986
PCT Pub. Date: Feb. 26, 2015

(30) Foreign Application Priority Data

Aug. 20, 2013 (EP) ..... 13181001

(51) Int. Cl.

| | |
|---|---|
| ***C12N 15/11*** | (2006.01) |
| ***A61K 31/713*** | (2006.01) |
| ***C12N 15/113*** | (2010.01) |
| ***A61K 31/7105*** | (2006.01) |
| ***G01N 33/574*** | (2006.01) |
| ***C12Q 1/68*** | (2018.01) |
| ***A61K 45/06*** | (2006.01) |
| ***C12Q 1/6886*** | (2018.01) |

(52) U.S. Cl.
CPC ..... *A61K 31/713* (2013.01); *A61K 31/7105* (2013.01); *A61K 45/06* (2013.01); *C12N 15/1135* (2013.01); *C12Q 1/6886* (2013.01); *G01N 33/5743* (2013.01); *C12N 2310/113* (2013.01); *C12N 2320/31* (2013.01); *C12Q 2600/112* (2013.01); *C12Q 2600/158* (2013.01)

(58) Field of Classification Search
CPC ..... C12N 2310/113; C12N 15/1135; C12N 2310/341
See application file for complete search history.

(56) References Cited

U.S. PATENT DOCUMENTS

| | | | | |
|---|---|---|---|---|
| 5,185,444 | A | 2/1993 | Summerton et al. | |
| 5,217,866 | A | 6/1993 | Summerton et al. | |
| 2009/0081658 | A1* | 3/2009 | Belouchi ..... | C12Q 1/6883 435/6.11 |
| 2013/0178428 | A1 | 7/2013 | Hoon | |

FOREIGN PATENT DOCUMENTS

| | | | |
|---|---|---|---|
| CN | 101633923 | A | 1/2010 |
| WO | 2007025085 | A2 | 3/2007 |
| WO | 2015024986 | A1 | 2/2015 |

OTHER PUBLICATIONS

Brown, Joseph W., et al. "Appraisal of the Consequences of the DDT-Induced Bottleneck on the Level and Geographic Distribution of Neutral Genetic Variation in Canadian Peregrine Falcons, Falco Peregrinus." Molecular Ecology, vol. 16, No. 2, 2007, pp. 327-343.
Chang et al., Lessons from Nature: microRNA-based shRNA libraries, Nature Methods 3, 707-714, 2006.
PCT International Search Report and Written Opinion, PCT Application No. PCT/EP20141067781, dated Feb. 12, 2014, 13 pages.
Chang et al. Nature Methods 3, 707-714, 2006.*
Brown et al. DDT 10, 595-601, 2005.*
Li et al., Downregulation of survivin expression enhances sensitivity of cultured uveal melanoma cells to cisplatin treatment, Experimental Eye Research, Apr. 11, 2006, pp. 176-182, vol. 83, No. 1, Academic Press Ltd, London.
Ulitsky et al., lincRNAs: Genomics, Evolution and Mechanisms, Cell, Jun. 25, 2013, pp. 26-46, vol. 154, No. 1, Cell Press, US.
MGC program team, Generation and initial analysis of more than 15,000 full-length human and mouse cDNA sequences, Proceedings of the National Academy of Sciences, Dec. 24, 2002, pp. 16899-16903, vol. 99, No. 26, National Academy of Sciences, US.
PCT International Search Report, PCT/EP2014/067781, dated Feb. 12, 2014.
PCT International Written Opinion, PCT/EP2014/067781, dated Feb. 12, 2014.
Leucci et al., Melanoma addiction to the long non-coding RNA SAMMSON, Mar. 24, 2016, Nature vol. 531, pp. 518-522, International Weekly Journal of Science.

* cited by examiner

*Primary Examiner* — Bruce R Campell
(74) *Attorney, Agent, or Firm* — Patent Law Works, LLP

(57) ABSTRACT

This disclosure relates to the field of cancer, particularly the field of melanoma. It was found that a particular long non-coding RNA (lncRNA) is specifically up-regulated in melanoma (but not other tumor) cells as compared to melanocytes. Inhibition of this lncRNA in melanoma cells leads to induction of apoptosis and is a novel therapeutic strategy in the treatment of melanoma.

15 Claims, 29 Drawing Sheets
(24 of 29 Drawing Sheet(s) Filed in Color)

Specification includes a Sequence Listing.

pPGK pPGK+GAP11

INHIBITION OF A LNCRNA FOR TREATMENT OF MELANOMA

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a national phase entry under 35 U.S.C. §371 of International Patent Application PCT/EP2014/067781, filed Aug. 20, 2014, designating the United States of America and published in English as International Patent Publication WO 2015/024986 A1 on Feb. 26, 2015, which claims the benefit under Article 8 of the Patent Cooperation Treaty to European Patent Application Ser. No. 1318100.2, filed Aug. 20, 2013.

TECHNICAL FIELD

This application relates to the field of cancer, particularly the field of melanoma. It was found that a particular long non-coding RNA (lncRNA) is specifically up-regulated in melanoma (but not other tumor) cells as compared to melanocytes. Inhibition of this lncRNA in melanoma cells leads to induction of apoptosis and is a novel therapeutic strategy in the treatment of melanoma.

BACKGROUND

Cutaneous malignant melanoma is the leading cause of skin cancer-related deaths. Its incidence is on the increase worldwide faster than any other cancer, with 5-year survival rates for patients with distant metastatic disease being less than 20%. Improvement of clinical outcomes for this aggressive, chemo- and radio-resistant disease remains a major clinical challenge. Significant progress in our understanding of the etiologies and genetic underpinnings of melanoma has nevertheless been made. These advances have recently led to promising results in trials of targeted therapies for this disease. The Ras/Raf/MEK/ERK pathway has been identified as the main regulator of cell proliferation in melanoma, with ERK being hyper-activated in up to 90% of human melanomas. Activating NRAS mutations are a common route to activating this pathway; mutations affecting codon 61 being the most prevalent (NRASQ61K). BRAF, one of the three human RAF genes, is also frequently mutated in melanomas, with the most common mutation being a glutamic acid for valine substitution at position 600 (V600E). BRAFV600E stimulates constitutive ERK signaling, leading to melanocyte hyper-proliferation. Early clinical experience with the novel class I RAF-selective inhibitor, PLX4032, demonstrated an unprecedented 80% anti-tumor response rate among patients with BRAFV600E-positive melanomas; unfortunately, patients acquire drug resistance within a few months of an initial response and combination therapies with MEK inhibitors are currently being investigated.

p53 pathway inactivation, which mainly arises as a consequence of inactivating mutations or allelic loss of the p53 gene itself, is the most common molecular defect in human cancers. Intriguingly, the p53 locus is intact in over 95% of melanoma cases, raising questions as to the pathogenic relevance of p53 in the etiology of melanoma tumor formation. At the same time, there is an increasing body of evidence supporting a relevant role for p53 in melanoma development. Loss of p53 cooperates with melanocyte-specific overexpression of activated HRASV12G and BRAFV600E in promoting melanomagenesis in mice and oncogenic NRAS cooperates with p53 loss to generate melanomas in zebrafish. Cancers that retain expression of wild-type p53 often find alternative ways to subvert p53 function, through either deregulation of upstream modulators and/or inactivation of downstream effectors. MDM2, which encodes an E3 ubiquitin ligase that controls p53 levels and function19, is amplified in human melanomas but only in 3%-5% of documented cases. Recently, MDM4 up-regulation has also been identified as a key determinant of impaired p53 function in human melanoma.

Other pathways that could become the targets of therapeutic interventions are the canonical Wnt signaling pathway and/or the transcriptional network regulated by the melanocyte lineage-specific transcription factor MITF. MITF induces gene expression patterns that prompt melanocytes to differentiate and initiate pigment production by activating genes important for melanin biosynthesis (such as Mc1r, Tyr, Dct and Trp-1) and melanosome formation (such as Pmel). Importantly, deregulation of MITF levels and/or of its transcriptional activity contributes to melanomagenesis. As such a rheostat model for MITF function was suggested in which higher expression of MITF is associated with proliferation and lower MITF levels with migration/invasion and senescence. Amplification/overexpression of MITF, found in 10%-20% of metastatic melanomas, correlates with decreased 5-year survival rates. One of the key pro-oncogenic functions of MITF relates to its ability to promote melanoma survival by promoting expression of the anti-apoptotic gene BCL-2. Wnt/β-catenin signaling directly regulates the expression of MITF and constitutive activation of Wnt/β-catenin signaling increases the proliferation of melanoma cells, accompanied by MITF-dependent increases in clonogenic growth, implicating this pathway as a promoter of melanoma progression.

Because of its ability to acquire drug resistance and chemoresistance and because melanoma is a highly dynamic and genetically heterogeneous tumor, novel treatment strategies and combination therapies are urgently needed. Several protein-coding therapeutic targets have indeed been identified for melanoma including components of the MAP-kinase pathway such as BRAFV600E, MEK and a modifier of the p53 pathway, MDM4. However, the targeting of these molecules remains only applicable in a restricted number of cases (e.g., against tumors that carry the BRAFV600E mutation or overexpress MDM4 and harbor wild-type TP53).

BRIEF SUMMARY

As one of the most virulent human cancers, melanoma is capable of distant and lethal metastases when the primary tumor volume is as little as 1 $mm^3$. Presently, there is a dearth of molecular markers that facilitate detecting the differences between benign and malignant melanocytic lesions and assist in predicting their biological behaviors.

Moreover, there is currently no effective long-term treatment for metastatic melanoma. Melanoma is driven by mutations (i.e., BRAFV600E, NRASQ61K) that activate mitogen-activated protein kinase (MAPK) signaling. Inactivation of MEK or ERK are very effective in killing melanoma cells; unfortunately, many normal cells also rely on MAPK signaling for their growth and survival, making MEK and ERK-inhibitors very toxic in patients.

Targeting activated BRAFV600E leads to unprecedented, dramatic and rapid tumor regression that relapses after some months, with resistance arising from activating mutations in other factors that bypass the requirement for activated BRAF in MAPK signaling. An alternative strategy that would bypass the genetic resistance arising from targeting specific components of the MAPK pathway and toxicity associated with MAPK inactivation in normal cells, would be to identify therapeutics that act on melanoma cells only (and not normal cells), irrespective of how MAPK signaling is activated.

Herein described is a long non-coding RNA, transcribed from the LINC01212 aka RP11-460N16.1 gene, which is expressed in the vast majority of melanoma (and not in normal/non-transformed melanocytes or other tumor types) and that is essential for melanoma cell survival, irrespective of how the MAPkinase is activated (BRAF or NRAS mutations or activation of MEK) and whether TP53 is wild-type or mutated.

Knock-down (KD) of the lncRNA induces apoptosis in melanoma cells independent of TP53 status (in contrast to, e.g., therapeutic inhibition of MDM4, which is only successful with wild-type TP53) and independent of how the MAPkinase pathway is activated.

Without being bound to a particular mechanism, it could be shown that LINC01212 KD leads to down-regulation of key components of the canonical Wnt pathway, MITF (and some of its targets such as DCT, TYRP1) and MEK1 and MEK2, concomitant with activation of the p53/p63 signaling pathway and induction of expression of key pro-apoptotic/tumor suppressor p53/p63 targets such as BAX, APAF-1, PUMA, GADD45A or PERP.

This offers significant potential in treating melanoma, also those melanomas not characterized by, e.g., the BRAF V600E mutation.

Provided are inhibitors of functional expression of the LINC01212 gene. Such inhibitors can act at the DNA level, or at the RNA (i.e., gene product) level. As LINC01212 is a non-coding gene, there is no protein product for this gene.

The inhibitors of functional expression of LINC01212 may be provided for use as a medicament. The inhibitors of functional expression of LINC01212 may be provided for use in treatment of cancer, in particular, skin cancer (e.g., BCC, SCC). The inhibitors may be provided for use in treatment of melanoma.

This is equivalent to saying that methods of treating melanoma in a subject in need thereof are provided, such methods comprising administering an inhibitor of functional expression of LINC01212 to the subject.

The nature of the inhibitor is not vital to the disclosure, as long as it inhibits the functional expression of the LINC01212 gene. According to specific embodiments, the inhibitor is selected from a gapmer, a shRNA, a siRNA, a CRISPR, a TALEN®, or a Zinc-finger nuclease.

According to alternative, but not exclusive, specific embodiments, the inhibitor selectively induces apoptosis in melanoma cells. This particularly implies that it induces apoptosis in melanoma cells, but not in normal (non-transformed) melanocytes. According to further specific embodiments, the inhibitor induces apoptosis independent of p53, BRAF, NRAS or MEK status, e.g., independent whether these proteins have particular mutations or not, or independent of their expression levels.

Even though inhibition of LINC01212 is sufficient to achieve a therapeutic effect, i.e., to achieve apoptosis in cancer cells, it is shown herein that a stronger, synergistic effect is achieved when both an inhibitor of LINC01212 and another chemotherapeutic are administered. This is particularly true for B-raf kinase inhibition.

According to a further aspect, methods are provided that may identify whether a tumor is suitable for treatment with an inhibitor of functional expression of LINC01212. These methods typically have the following steps:

Determining whether expression of LINC01212 is increased in the tumor or a sample of tumor cells;

Establishing whether the tumor is suitable for treatment, wherein increased expression is indicative of suitability for treatment.

The increase in expression is typically compared to a suitable control, e.g., a population of control cells, such as, but not limited to, skin cells or non-transformed melanocytes. Of note, if the control does not express LINC01212, then the mere presence of LINC01212 RNA in the sample is equivalent to increased expression.

The methods thus may entail a first step of providing a sample of tumor cells. The determining step may occur purely in vitro, i.e., without a step interacting on the human or animal body.

According to particular embodiments, the tumor is melanoma.

According to specific embodiments, when it is established that the tumor is suitable for treatment, the methods may further comprise a step of administering an inhibitor of functional expression of LINC01212 to the subject in which the tumor is present. This is in order to treat the tumor.

Also provided herein are methods of diagnosing the presence of melanoma in a subject, comprising the steps of:

Determining the levels of LINC01212 in a sample of the subject;

Correlating the levels of LINC01212 in the sample with the presence of melanoma.

In such methods, the presence (or increased expression) of LINC01212 is indicative of the presence of melanoma in the subject from whom the sample is taken. Typically, these methods are performed in vitro, although in vivo methods are not necessarily excluded. Determining the levels of LINC01212 will typically be done by determining the levels of LINC01212 RNA in the sample.

The sample can be a tissue sample (e.g., a skin biopt), but as is shown herein, in melanoma patients, LINC01212 also circulates in the blood. Thus, it can also be detected in blood or serum, and the sample can be a blood sample or a serum sample.

The levels of LINC01212 RNA vary with different stages of the disease (FIG. 6). Accordingly, in methods that determine the presence of melanoma, a further step may be included that correlates the levels of LINC01212 to disease severity, disease stage (e.g., stage of melanoma), or disease progression.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Definitions

Figure 1:
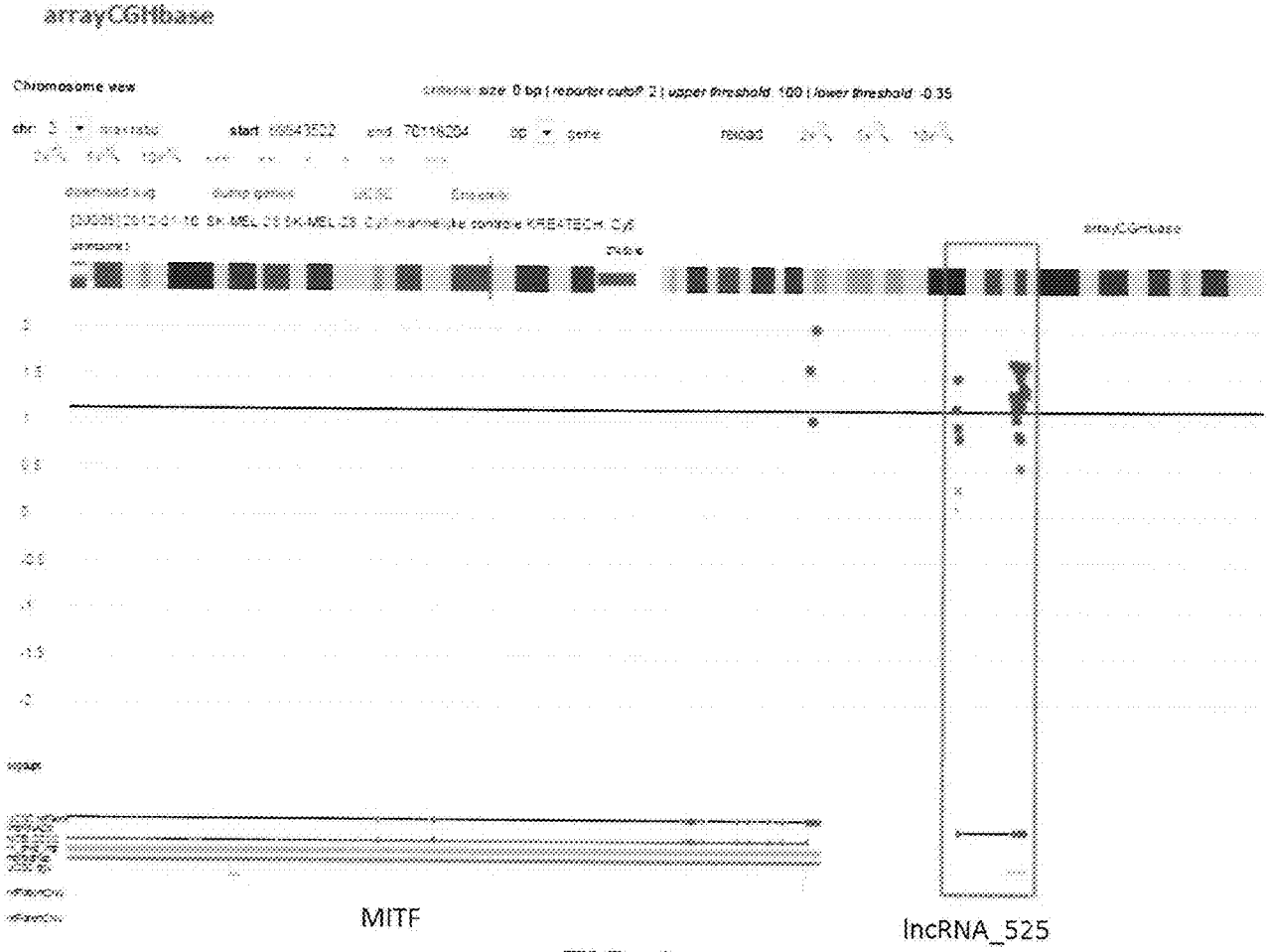
FIG. 1 shows an arrayCGH analysis of the long transcript of the LINC01212 gene, downstream of the MITF locus.

This disclosure will be described with respect to particular embodiments and with reference to certain drawings, but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated.

Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of this disclosure. Practitioners are particularly directed to Sambrook et al., Molecular Cloning: A Laboratory Manual, $2^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

The term "LINC01212," "long intergenic non-protein coding RNA 1212," or "RP11-460N16.1," as used herein, refers to the gene with accession number ENSG00000240405 in Ensembl, as well as the mRNA that is transcribed from the gene. It can also be identified with Gene ID: 101927152 or the human gene nomenclature identifier HGNC: 49644. As it is a non-protein coding gene, there is no protein product. In humans, the gene is located on the short arm of chromosome 3, from position 70,048,728 to 70,064,469. The gene has two annotated transcripts (or splice variants): LINC01212-001 (transcript ID ENST00000483525 in Ensembl) with a length of 2044 bp, and LINC01212-002 (transcript ID ENST00000488861 in Ensembl) with a length of 513 bp. Both transcripts are lincRNA (large intergenic non-coding RNAs), their respective consensus sequences are (SEQ ID NO: 1

CTGAAGTCGCTAGACATTTGAGGAACACATCCGGG

GAAGAAGACACAGGTGGCTGGTCATGGAGAGCCCGCTGGGGGAAGAGCAC

ACAGACAGGCACCGGCAGGCCATTGACCAGCGGGACAAGGIGGGCTCAAT

GTCATCACAAGGGTGCTTAAGAGGGAAAGAGGAAGCCATGAGGGTCAGAG

TCAAAGGAAGACTTGAAGATACTACACTGCGGACTTTAAAGATGAAGGAA

GGGGCOAAAACCAAGAATGTGGGAAGCCTCTAGAAGCTAGAGAAGGCAAG

GAAACAAATTTTCCACTAGAGCCTCCAGAAGGAACACAGCCCTGCTGACC

CACTGTAATGTCTGACCTCTAGATGTGTAAGGGTAGTAAGACTGAAAGTC

TCAGAAAGGCACTGTTAAATTCTTATTCCTCAACTATGCAACTCAAAACT

GGGGTCCTCAGCAGTGAGCGAGGGGTGAGAGAAGACACTGTATAAACATG

GCACATCCTCCTGGAAAGTCAACTTTACTCAAAGCTTTAGAAACCCAGCT

CAAACTAGCTGAAGCAGAAAAGACATTACTGCGCCTATAAGTTGAAACTT

TGGAGGGATAAATTTCAGAGGTGTGGCTAGATCCAACGGCTCTCTGGAAA

ACTCTGTGAAAAAAATGCTTCCTCAAGTCCAGAAACCAGAAGCTCAGGAA

ATTGTTGCTTGGTTCCTCTTGTTAGAGGCAGAGATTATTCAACGACCTAC

AGGGTAGCGTTTGAACATTGTTACCAGGAATCTTTACTTTGCCATCTICC

AAGTCTGTTCTCCTCAGTATTGGTTTCATTTACAAGCAGGCCATCTCTGC

CCTCATGGCAATGATGGTCTTTACTCCAGGCTTAAGACCCTTACTATCTA

CTATTTCCAAAGCGGAGAGAGAACTTCCCACACCTAGTGACCTGTGACAC

AGGATTTTATCCTTCGTACAGAGGGAATTCAGTTGGCTAACATAATCTGC

-continued

CTTCCAATOGAGTAAGAATGTCTGGACTCTTTCCTTCACCTACCCCCAAG

ACATGGAGGCGTCTAAAAGATAAATAAAACTTGGCAACTGACCGAAGGAG

GAAGAGGGGATTTCAGGCAAAATCAACGCTGTTCACTACGAGGAGACTTC

AGAAAGGTTGCCTGCTTCTGGGGAGCATAGTCCCTGATTCCTCAAGACAT

ACGTTTATTCTTTTCTTCAATGTCTTTGCCTGCAGTCAAAACAAAACCAT

TACCTTTAGCCAAGTICACACATTTCAGCCAAATCCATATGCATCGGATC

AGTTCTGTAGGTTATGGGTGAGCATGAACATATAAAAGAGGCACCTGCCT

GTGCCTATCTACTCCATGGAATTTCAAAAGGGGCCACTTATGGAGAATGT

CTTTAGGGACAGAACCAACCACCCTGTCTTTCCTCCAACTCTCAAAGTAA

CTTCTGGCTTTAATCCTCAAGTGTCTATGCTGGAGTTTAAGAAAAATGTT

TTTCATAGAATTCATGTGTATGATATTGCATGAGTTGTCCATCTTTGTAT

ATATCTCAAGACTTGTGGTGTTAGTTAAAGATTCAGAGCTCTGTGTCCTG

AACACAGAGTAATACCAGCATTACTAAGGATGATCGTGGGATTTTAAAAT

TCCTCCCTTAGATAGATCTTACGAACTTATGTTACCAATCAACATAAGTT

AAGACAAAAAGAGCAAATTTAGATGTAAAACCATCTTGGGGCCAGGIGCT

GTGGCTCACGCCTGTAATCCCAGCACTTTGGGAGGCCGAGGCGGGCGGAT

CACTAGGTCAGGAGATCGAGACCATCTTGGCCAACACGGTGAAACCCTGT

CTCTACTAAAAATACAAAAAAATTAGCCGGGCATGGTGGCAGGCGCCTGT

AGTCCCAGCTACTAGGGAGGCTGAGGCAGGAGAATGGTGTGAACCCTGGA

AGCGGAGCTTGCAGTGAGCCAAGATCATGCCACTGCACTGCAGCTTGGGC

GACAGAGCGAGACTCCGTCTCAAAAAAAACCAAACCAACAAACAAACAAA

CAAAAAAAA of the Sequence Listing incorporated herein) and (SEQ ID NO: 2)

GAGGAAGGCGGGTCCCTGGCTCGGCTCTACCCCCATGGATCTAGGTGGG

CTCAATGTCATCACAAGGGTGCTTAAGAGGGAAAGAGGAAGCCATGAGG

GTCAGAGTCAAAGGAAGACTTGAAGATACTACACTGCGGACTTTAAAGA

TGAAGGAAGGGGCGAAAACCAAGAATGTGGGAAGCCTCTAGAAGCTAGA

GAAGGCAAGGAAACAAATTTTCCACTAGAGCCTCCAGAAGGAACACAGC

CCTGCTGACCCACTGTAATGTCTGACCTCTAGATGTGTAAGGGTAGTAA

GACTGAAAGTCTCAGAAAGGCACTGTTAAATTCTTATTCCTCAACTATG

CAACTCAAAACTGGGGTCCTCAGCAGTGAGCGAGGGGTGAGAGAAGACA

CTGTATAAACATGGCACATCCTCCTGGAAAGTCAACTTTACTCAAAGCT

TTAGAAACCCAGCTCAAACTAGCTGAAGCAGAAAAGACATTACTGCGCC

TATAAGTTGAAACTTTGGAGGGA.

Note, however, that, for both sequences, variations in the non-coding exons have been reported in dbSNP, and these variations are envisaged as belonging to the respective transcript IDs. That is, unless specifically mentioned otherwise, the term RP11460N16.1 (or LINC01212) encompasses the different isoforms.

Moreover, analysis of publicly available RNA-seq data from TCGA as well as in-house RNA-seq data from short-term melanoma cultures indicate the presence of additional exons located 3' from the annotated LINC01212 exons. In silico-based reconstitution of the transcript indicates that the full-length isoform is 4063 bp in length.

The sequence of this isoform is:

(SEQ ID NO: 3)

CTGAAGTCGCTAGACATTTGAGGAAC

ACATCCGGGGAAGAAGACACAGGTGGCTGGTCATGGAGAGCCCGCTGGGG

GAAGAGGACAGAGAGAGGOAcoOOGAGoocATTOAGOAGGOODAGAAGGT

GGGCTCAATGTCATCACAAGGGTGCTTAAGAGGGAAAGAGGAAGCCATGA

GGGTCAGAGTCAAAGGAAGACTTGAAGATACTACACTGCGGACTTTAAAG

ATGAAGGAAGGGGCGAAAACCAAGAATGTGGGAAGCCTCTAGAAGCTAGA

GAAGGCAAGGAAACAAATTTTCCACTAGAGCCTCCAGAAGGAACACAGCC

CTGCTGACCCACTGTAATGTCTGACCTCTAGATGTGTAAGGGTAGTAAGA

CTGAAAGTCTCAGAAAGGCACTGTTAAATTCTTATTCCTCAACTATGCAA

CTCAAAACTGGGGTCCTCAGCAGTGAGCGAGGGGTGAGAGAAGACACTGT

ATAAACATGGCACATCCTCCTGGAAAGTCAACTTTACTCAAAGCTTTAGA

AACCCAGCTCAAACTAGCTGAAGCAGAAAAGACATTACTGCGCCTATAAG

TTGAAACTTTGGAGGGATAAATTTCAGAGGTGTGGCTAGATCCAACGGCT

CTCTGGAAAACTCTGTGAAAAAAATGCTTCCTCAAGTCCAGAAACCAGAA

GCTCAGGAAATTGTTGCTTGGTTCCTCTTGTTAGAGGCAGAGATTATTCA

ACGACCTACAGGGTAGCGTTTGAACATTGTTACCAGGAATCTTTACTTTG

CCATCTTCCAAGTCTGTTCTCCTCAGTATTGGTTTCATTTACAAGCAGGC

CATCTCTGCCCTCATGGCAATGATGGTCTTTACTCCAGGCTTAAGACCCT

TACTATCTACTATTTCCAAAGCGGAGAGAGAACTTCCCACACCTAGTGAC

CTGTGACACAGGATTTTATCCTTCGTACAGAGGGAATTCAGTTGGCTAAC

ATAATCTGCCTTCCAATGGAGTAAGAATGTCTGGACTCTTTCCTTCACCT

ACCCCCAAGACATGGAGGCGTCTAAAAGATAAATAAAACTTGGCAACTGA

CCGAAGGAGGAAGAGGGGATTTCAGGCAAAATCAACGCTGTTCACTACGA

GGAGACTTCAGAAAGGTTGCCTGCTTCTGGGGAGCATAGTCCCTGATTCC

TCAAGACATACGTTTATTCTTTTCTTCAATGTCTTTGCCTGCAGTCAAAA

CAAAACCATTACCTTTAGCCAAGTTCACACATTTCAGCCAAATCCATATG

CATCGGATCAGTTCTGTAGGTTATGGGTGAGCATGAACATATAAAAGAGG

CACCTGCCTGTGCCTATCTACTCCATGGAATTTCAAAAGGGGCCACTTAT

GGAGAATGTCTTTAGGGACAGAACCAACCACCCTGTCTTTCCTCCAACTC

TCAAAGTAACTTCTGGCTTTAATCCTCAAGTGTCTATGCTGGAGTTTAAG

AAAAATGTTTTTCATAGAATTCATGTGTATGATATTGCATGAGTTGTCCA

TCTTTGTATATATCTCAAGACTTGTGGTGTTAGTTAAAGATTCAGAGCTC

TGTGTCCTGAACACAGAGTAATACCAGCATTACTAAGGATGATCGTGGGA

TTTTAAAATTCCTCCCTTAGATAGATCTTACGAACTTATGTTACCAATCA

ACATAAGTTAAGACAAAAAGAGCAAATTTAGATGTAAAACCATCTTGGGG

CCAGGTGCTGTGGCTCACGCCTGTAATCCCAGCACTTTGGGAGGCCGAGG

CGGGCGGATCACTAGGTCAGGAGATCGAGACCATCTTGGCCAACACGGTG

-continued

AAACCCTGTCTCTACTAAAAATACAAAAAAATTAGCCGGGCATGGTGGCA

GGCGCCTGTAGTCCCAGCTACTAGGGAGGCTGAGGCAGGAGAATGGTGTG

AACCCTGGAAGCGGAGCTTGCAGTGAGCCAAGATCATGCCACTGCACTGC

AGCTTGGGCGACAGAGCGAGACTCCGTCTCAAAAAAAACCAAACCAACAA

ACAAACAAACAAAAAAAAGCACATTGAAAATGACATGATCTATCCCAAGG

AATAGCTTAAGACCTGATCCACTTAAACAGCTCCAAGTGATTTATCATAA

ATGTGCTTATTTGGAAGGTTTAGCAGTAACCGCTTATGGGAGGTGGTGGG

GTTAACTACCAAAATTGTACATAACTTGGATCCTGTGTATGGCAATTAAT

CAAGAAATTATATTCTTTGACTTTCTAACAACCCACACAGAGTGCTACAT

CTGTGGCATGTTTAAAGAGAGAGCGAGGGATGAAATATTTCTTCTAATAA

AATGCTAATGGCTTTGTTTTGGAGAAAAAATATTGGATTATTGTGGTGTT

AGATTTATCTGTATGAGGATTTCTCGAGTCACAGTCAGTAAGTACTTCTG

ACAGAAAACCAGCTATGTCCTGAATACAATATCCCAGTCTTCTAAATGAC

TTCAGGATTATGGAGAGGCCCCTTTATAATACTGAAGAAAGAACACAGGA

ATAAATGGTGTGATAGAGAACTGTAGCAGTCGAAGTTATTACTGTGAGCA

TTTGTTAAATGTTCAAGAGTATTTATTTAACCCAAAGCACATTGGAATAT

GTTAATTAAGACAGGTGAGGCATCCCATTGATTTGTGGTGTCTCATGGGC

ATAACTTGCACCCACTTAGTTGCTCTAGTCCTTAGGTTTTCAAGATTTTG

CGGGGATGCCTACTGTGGTTAGGAACCCAGAGCTCACTCCTTGGAGGGTT

AGTTTCACAAATTCAATATCTGAAAACCTAAAAGTACCATCATCTAAAAA

GAAAAATTTGGGGCAACAAAAGCGCCAAAGTATAATGTCATTTTCATTCC

TATGATCCTTTGTGATGTGGTTCAAATGGCTTATTTTAATATTTCACTTT

TCAATCAGTAGCTTTTTAAAAATGACAATTTCACAAATGCTTATGGAGCA

TCTACTTTGTGCCTACACTGGCCAAGAGACAGAAAGATGGAATAATACCT

GACTTCTACCTTTTAAGATCTCATAGTGCAGCAAAACAGAGAGCTGTAGC

AAATATTTGTAATGTGAAAAGAGCAACACTCATGAAACAGTCCAGTGCTG

GACACTTACTGTAGTAGAGACACTGCATCAATGATTCTCTTTTACAGGCA

AGGGAACTGAAGCTTGTAGAGAGGTTAGATCACACAGTTAACAAGAAGAG

GGACAAGCATTTACCGGAAGCCCTGTGTGGTTCTGGATACTCACATAGTG

CTTGCCAGACGCCCGGCATTGTGTTTAGGGCTTTACACTCATGACCTCAC

TCGGTCCTCATGACAACCCTATGCAGGGGATACTATAATTATCCCCATTT

CACAGATGAGCAAACTGAGCTCTGAGAAGGAGCAACTTGACCAAGGTCAT

GTAGGTAATGTCAGAGCAGCAATTTGAATATAGGCTCTTGACAACTAAAC

TTTACTGCTGTGAGATGTAGAGGCATTTCTGCCTGGAGCTGCGGGAAGGT

ACAGAGATTAGGGCAAATAAATTATAAGAAGATTAGAAATATGGTCTTGA

TAAGGACTTTGAAGATAATGCTTATATCAGACTTCCTTCTGATCTGAGTC

AATTGAAGGATGTATTTTTGAACCTTTCAGAAATCTCTCTATAAGTTATA

GATCTGAATTTTAGTGAGAATCTATTCCATTCCTCGGAGTGCGAAAATCC

AACACAATGTCTGGGAATTCAGACTTATAAAAATCATACAGAAGTAATTC

TTAAAAAATCTTTTATTTTGAAGTAATTGTAGGCTCATAAGAGGTTGTAA

AAATAAGAGAGTTATAGTATGCCCTTCACCCAGCTTCCTCCAAAGTTAAC

-continued

GTTTTATATAACCATAGTACATATCAAAAGTGGGAAATAGACTTTGACAA

AATACTATTCATTAGACCACAGATCATATGGGGATTTCATTAGTTTTTAG

ATGCACTCTATTGTTTTGTATAGTTCTTTTCCATTTTATCACCTGTATAG

ATTTGTGTAACCACCAAGAAGTAATTTGTTTTAAGCT.

According to particular embodiments, the LINC01212 gene product refers to the long transcript, i.e., ENST00000483525, or the longer isoform (as exemplified by SEQ ID NOS:2 and 3).

With "functional expression" of LINC01212, it is meant the transcription and/or translation of functional gene product. For non-protein coding genes like LINC01212, "functional expression" can be deregulated on at least two levels. First, at the DNA level, e.g., by absence or disruption of the gene, or lack of transcription taking place (in both instances, preventing synthesis of the relevant gene product). The lack of transcription can, e.g., be caused by epigenetic changes (e.g., DNA methylation) or by loss of function mutations. A "loss-of-function" or "LOF" mutation as used herein is a mutation that prevents, reduces or abolishes the function of a gene product as opposed to a gain-of-function mutation that confers enhanced or new activity on a protein. LOF can be caused by a wide range of mutation types, including, but not limited to, a deletion of the entire gene or part of the gene, splice site mutations, frame-shift mutations caused by small insertions and deletions, nonsense mutations, missense mutations replacing an essential amino acid and mutations preventing correct cellular localization of the product. Also included within this definition are mutations in promoters or regulatory regions of the LINC01212 gene if these interfere with gene function. A null mutation is an LOF mutation that completely abolishes the function of the gene product. A null mutation in one allele will typically reduce expression levels by 50%, but may have severe effects on the function of the gene product. Note that functional expression can also be deregulated because of a gain of function mutation: by conferring a new activity on the protein, the normal function of the protein is deregulated, and less functionally active protein is expressed. Vice versa, functional expression can be increased, e.g., through gene duplication or by lack of DNA methylation.

Second, at the RNA level, e.g., by lack of efficient translation taking place because of destabilization of the mRNA (e.g., by UTR variants) so that it is degraded before translation occurs from the transcript, or by lack of efficient transcription, e.g., because a mutation introduces a new splicing variant.

The term "status" as used in the application with regard to a particular protein, specifically tumor-associated proteins (e.g., p53 status, BRAF status, NRAS status, MEK status, . . . ) refers to the mutational status and/or the expression of these particular proteins. Typically, the term is used in the sense "irrespective of" or "independent of" status, meaning that an effect is observed irrespective of expression levels of, or presence of mutations in, the particular protein.

"Long non-coding RNAs" (long ncRNAs, lncRNA) as used herein are non-protein coding transcripts longer than 200 nucleotides. A particular class of lncRNA are long intergenic ncRNAs (lincRNA), referring to long non-coding RNAs that are transcribed from non-coding DNA sequences between protein-coding genes.

The disclosure is the first to show specific expression of lncRNAs in melanoma, and that inhibition of such lncRNA can be used to selectively induce apoptosis in these cancer cells.

Provided are inhibitors of functional expression of the LINC01212 gene. Such inhibitors can act at the DNA level, or at the RNA (i.e., gene product) level. As LINC01212 is a non-coding gene, there is no protein product for this gene.

If inhibition is to be achieved at the DNA level, this may be done using gene therapy to knock-out or disrupt the target gene. As used herein, a "knock-out" can be a gene knock-down or the gene can be knocked out by a mutation such as, a point mutation, an insertion, a deletion, a frameshift, or a missense mutation by techniques known in the art, including, but not limited to, retroviral gene transfer. Another way in which genes can be knocked out is by the use of zinc finger nucleases. Zinc-finger nucleases (ZFNs) are artificial restriction enzymes generated by fusing a zinc finger DNA-binding domain to a DNA-cleavage domain. Zinc finger domains can be engineered to target desired DNA sequences, which enable zinc-finger nucleases to target unique sequence within a complex genome. By taking advantage of endogenous DNA repair machinery, these reagents can be used to precisely alter the genomes of higher organisms. Other technologies for genome customization that can be used to knock out genes are meganucleases and TAL effector nucleases (TALENs, Cellectis bioresearch). A TALEN® is composed of a TALE DNA binding domain for sequence-specific recognition fused to the catalytic domain of an endonuclease that introduces double-strand breaks (DSB). The DNA binding domain of a TALEN® is capable of targeting with high precision a large recognition site (for instance, 17 bp). Meganucleases are sequence-specific endonucleases, naturally occurring "DNA scissors," originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes).

Another recent genome editing technology is the CRISPR/Cas system, which can be used to achieve RNA-guided genome engineering. CRISPR interference is a genetic technique that allows for sequence-specific control of gene expression in prokaryotic and eukaryotic cells. It is based on the bacterial immune system-derived CRISPR (clustered regularly interspaced palindromic repeats) pathway.

Gene inactivation, i.e., inhibition of functional expression of the gene, may, for instance, also be achieved through the creation of transgenic organisms expressing antisense RNA, or by administering antisense RNA to the subject. An antisense construct can be delivered, for example, as an expression plasmid, which, when transcribed in the cell, produces RNA that is complementary to at least a unique portion of the cellular LINC01212 lncRNA.

A more rapid method for the inhibition of gene expression is based on the use of shorter antisense oligomers consisting of DNA, or other synthetic structural types such as phosphorothiates, 2'-0-alkylribonucleotide chimeras, locked nucleic acid (LNA), peptide nucleic acid (PNA), or morpholinos. With the exception of RNA oligomers, PNAs and morpholinos, all other antisense oligomers act in eukaryotic cells through the mechanism of RNase H-mediated target cleavage. PNAs and morpholinos bind complementary DNA and RNA targets with high affinity and specificity, and thus act through a simple steric blockade of the RNA translational machinery, and appear to be completely resistant to nuclease attack. An "antisense oligomer" refers to an antisense molecule or anti-gene agent that comprises an oligomer of at least about 10 nucleotides in length. In some embodiments, an antisense oligomer comprises at least 15, 18, 20, 25, 30, 35, 40, or 50 nucleotides. Antisense approaches involve the design of oligonucleotides (either DNA or RNA, or derivatives thereof) that are complementary to an RNA encoded by polynucleotide sequences of LINC01212. Antisense RNA may be introduced into a cell to inhibit translation of a complementary mRNA by base pairing to it and physically obstructing the translation machinery. This effect is, therefore, stoichiometric. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense polynucleotide sequences, a single strand of the duplex DNA may thus be tested, or triplex formation may be assayed. The ability to hybridize will depend on both the degree of complementarity and the length of the antisense polynucleotide sequence. Generally, the longer the hybridizing polynucleotide sequence, the more base mismatches with an RNA it may contain and still form a stable duplex (or triplex, as the case may be). One skilled in the art can ascertain a tolerable degree of mismatch by use of standard procedures to determine the melting point of the hybridized complex. Antisense oligomers should be at least ten nucleotides in length, and are preferably oligomers ranging from 15 to about 50 nucleotides in length. In certain embodiments, the oligomer is at least 15 nucleotides, at least 18 nucleotides, at least 20 nucleotides, at least 25 nucleotides, at least 30 nucleotides, at least 35 nucleotides, at least 40 nucleotides, or at least 50 nucleotides in length. A related method uses ribozymes instead of antisense RNA. Ribozymes are catalytic RNA molecules with enzyme-like cleavage properties that can be designed to target specific RNA sequences. Successful target gene inactivation, including temporally and tissue-specific gene inactivation, using ribozymes has been reported in mouse, zebrafish and fruitflies. RNA interference (RNAi) is a form of post-transcriptional gene silencing. The phenomenon of RNA interference was first observed and described in Caenorhabditis elegans where exogenous double-stranded RNA (dsRNA) was shown to specifically and potently disrupt the activity of genes containing homologous sequences through a mechanism that induces rapid degradation of the target RNA. Several reports describe the same catalytic phenomenon in other organisms, including experiments demonstrating spatial and/or temporal control of gene inactivation, including plant (Arabidopsis thaliana), protozoan (Trypanosoma bruceii), invertebrate (Drosophila melanogaster), and vertebrate species (Danio rerio and Xenopus laevis). The mediators of sequence-specific messenger RNA degradation are small interfering RNAs (siRNAs) generated by ribonuclease III cleavage from longer dsRNAs. Generally, the length of siRNAs is between 20-25 nucleotides (Elbashir et al. (2001) Nature 411, 494-498). The siRNA typically comprises a sense RNA strand and a complementary antisense RNA strand annealed together by standard Watson Crick base pairing interactions (hereinafter "base paired"). The sense strand comprises a nucleic acid sequence that is identical to a target sequence contained within the target mRNA. The sense and antisense strands of the present siRNA can comprise two complementary, single-stranded RNA molecules or can comprise a single molecule in which two complementary portions are base paired and are covalently linked by a single-stranded "hairpin" area (often referred to as shRNA). The term "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

The siRNAs of the disclosure can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the disclosure can also comprise a 3' overhang. A "3' overhang" refers to at least one unpaired nucleotide extending from the 3' end of an RNA strand. Thus, in one embodiment, the siRNA of the disclosure comprises at least one 3' overhang from one to about six nucleotides (which includes ribonucleotides or deoxynucleotides) in length, preferably from one to about five nucleotides in length, more preferably from one to about four nucleotides in length, and particularly preferably from about one to about four nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is two nucleotides in length. In order to enhance the stability of the present siRNAs, the 3' overhangs can also be stabilized against degradation. In one embodiment, the overhangs are stabilized by including purine nucleotides, such as adenosine or guanosine nucleotides.

Alternatively, substitution of pyrimidine nucleotides by modified analogues, e.g., substitution of uridine nucleotides in the 3' overhangs with 2' deoxythymidine, is tolerated and does not affect the efficiency of RNAi degradation. In particular, the absence of a 2' hydroxyl in the 2' deoxythymidine significantly enhances the nuclease resistance of the 3' overhang in tissue culture medium.

The siRNAs of the disclosure can be targeted to any stretch of approximately 19 to 25 contiguous nucleotides in any of the target LINC01212 RNA sequences (the "target sequence"), of which examples are given in the disclosure. Techniques for selecting target sequences for siRNA are well known in the art. Thus, the sense strand of the present siRNA comprises a nucleotide sequence identical to any contiguous stretch of about 19 to about 25 nucleotides in the target mRNA.

The siRNAs of the disclosure can be obtained using a number of techniques known to those of skill in the art. For example, the siRNAs can be chemically synthesized or recombinantly produced using methods known in the art. Preferably, the siRNA of the disclosure are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA of the disclosure from a plasmid include, for example, the U6 or H1 RNA pol III promoter sequences and the cytomegalovirus promoter. Selection of other suitable promoters is within the skill in the art. The recombinant plasmids of the disclosure can also comprise inducible or regulatable promoters for expression of the siRNA in a particular tissue or in a particular intracellular environment. The siRNA expressed from recombinant plasmids can either be isolated from cultured cell expression systems by standard techniques, or can be expressed intracellularly, e.g., in breast tissue or in neurons.

The siRNAs of the disclosure can also be expressed intracellularly from recombinant viral vectors. The recombinant viral vectors comprise sequences encoding the siRNAs of the disclosure and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the disclosure can also comprise inducible or regulatable promoters for expression of the siRNA in the tissue where the tumor is localized.

As used herein, an "effective amount" of the siRNA is an amount sufficient to cause RNAi-mediated degradation of the target mRNA, or an amount sufficient to inhibit the progression of metastasis in a subject. RNAi-mediated degradation of the target mRNA can be detected by measuring levels of the target mRNA or protein in the cells of a subject, using standard techniques for isolating and quantifying mRNA or protein as described above.

One skilled in the art can readily determine an effective amount of the siRNA of the disclosure to be administered to a given subject, by taking into account factors such as the size and weight of the subject; the extent of the disease penetration; the age, health and sex of the subject; the route of administration; and whether the administration is regional or systemic. Generally, an effective amount of the siRNA of the disclosure comprises an intracellular concentration of from about 1 nanomolar (nM) to about 100 nM, preferably from about 2 nM to about 50 nM, more preferably from about 2.5 nM to about 10 nM. It is contemplated that greater or lesser amounts of siRNA can be administered.

Recently it has been shown that morpholino antisense oligonucleotides in zebrafish and frogs overcome the limitations of RNase H-competent antisense oligonucleotides, which include numerous non-specific effects due to the non-target-specific cleavage of other mRNA molecules caused by the low stringency requirements of RNase H. Morpholino oligomers, therefore, represent an important new class of antisense molecule. Oligomers of the disclosure may be synthesized by standard methods known in the art. As examples, phosphorothioate oligomers may be synthesized by the method of Stein et al. (1988) Nucleic Acids Res. 16:3209-3210), methylphosphonate oligomers can be prepared by use of controlled pore glass polymer supports (Sarin et al. (1988) Proc. Natl. Acad. Sri. U.S.A. 85:7448-7451). Morpholino oligomers may be synthesized by the method of Summerton and Weller in U.S. Pat. Nos. 5,217,866 and 5,185,444.

Another particular form of antisense RNA strategy are gapmers. A gapmer is a chimeric antisense oligonucleotide that contains a central block of deoxynucleotide monomers sufficiently long to induce RNase H cleavage. The central block of a gapmer is flanked by blocks of 2'-O modified ribonucleotides or other artificially modified ribonucleotide monomers such as bridged nucleic acids (BNAs) that protect the internal block from nuclease degradation. Gapmers have been used to obtain RNase-H-mediated cleavage of target RNAs, while reducing the number of phosphorothioate linkages. Phosphorothioates possess increased resistance to nucleases compared to unmodified DNA. However, they have several disadvantages. These include low binding capacity to complementary nucleic acids and non-specific binding to proteins that cause toxic side-effects limiting their applications. The occurrence of toxic side-effects, together with non-specific binding causing off-target effects, has stimulated the design of new artificial nucleic acids for the development of modified oligonucleotides that provide efficient and specific antisense activity in vivo without exhibiting toxic side-effects. By recruiting RNase-H, gapmers selectively cleave the targeted oligonucleotide strand. The cleavage of this strand initiates an antisense effect. This approach has proven to be a powerful method in the inhibition of gene functions and is emerging as a popular approach for antisense therapeutics. Gapmers are offered commercially, e.g., LNA longRNA GapmeRs by Exiqon, or MOE gapmers by Isis pharmaceuticals. MOE gapmers or "2'MOE gapmers" are an antisense phosphorothioate oligonucleotide of 15-30 nucleotides wherein all of the backbone linkages are modified by adding a sulfur at the non-bridging oxygen (phosphorothioate) and a stretch of at least ten consecutive nucleotides remain unmodified (deoxy sugars) and the remaining nucleotides contain an O'-methyl O'-ethyl substitution at the 2' position (MOE).

According to a further aspect, the inhibitors of functional expression of LINC01212 are provided for use as a medicament. According to yet further aspects, the inhibitors of functional expression of LINC01212 are provided for use in treatment of cancer, in particular, skin cancer. In still further embodiments, the inhibitors are provided for use in treatment of melanoma.

This is equivalent to saying that methods of treating melanoma in a subject in need thereof are provided, such methods comprising administering an inhibitor of functional expression of LINC01212 to the subject.

The nature of the inhibitor is not vital to the disclosure, as long as it inhibits the functional expression of the LINC01212 gene. According to specific embodiments, the inhibitor is selected from an inhibitory RNA technology (such as a gapmer, a shRNA, a siRNA), a CRISPR, a TALEN®, or a Zinc-finger nuclease.

According to alternative, but not exclusive, specific embodiments, the inhibitor selectively induces apoptosis in melanoma cells. This particularly implies that it induces apoptosis in melanoma cells, but not in normal (non-transformed) melanocytes. According to further specific embodiments, the inhibitor induces apoptosis independent of p53, BRAF, NRAS or MEK status, e.g., independent of whether these proteins have particular mutations or not, or independent of their expression levels.

Even though inhibition of LINC01212 is sufficient to achieve a therapeutic effect, to achieve apoptosis in cancer cells, it is shown herein that a stronger, synergistic effect is achieved when both an inhibitor of LINC01212 and another chemotherapeutic are administered. This is particularly true for B-raf kinase inhibition (Example 3, FIG. 16). However, without being bound to a particular mechanism, the fact that LINC01212 inhibition induces apoptosis of melanoma cells independent of B-raf, N-ras or p53 status, as well as results in inhibition of all known survival pathways (see Example 4), indicates that this synergistic effect will be observed for other chemotherapeutics as well (particularly those therapeutics that interact with those targets or are sensitive to resistance using the survival pathways). Thus, other chemotherapeutics such as MEK inhibitors, cisplatin and melphalan are also explicitly envisaged. Additionally, the chemotherapeutic that can be used to obtain a synergistic effect can be one or more chemotherapeutic agents selected from a microtubule active agent, an alkylating agent, an antineoplastic anti-metabolite, a platin compound, a Raf or MEK kinase inhibitor, a topoisomerase I inhibitor, a topoisomerase H inhibitor, a VEGF inhibitor, a PI3/AKT kinase inhibitor, a tyrosine kinase inhibitor, an EGFR kinase inhibitor, an mTOR kinase inhibitor, an insulin-like growth factor I inhibitor, an HDAC inhibitor, a proteasome inhibitor, and ionizing radiation. The synergistic effect can be obtained through simultaneous, concurrent, separate or sequential use for preventing or treating melanoma.

Methods are provided that may identify whether a tumor is suitable for treatment with an inhibitor of functional expression of LINC01212. These methods typically have the following steps:

Determining whether expression of LINC01212 is increased in the tumor or a sample of tumor cells;

Establishing whether the tumor is suitable for treatment, wherein increased expression is indicative of suitability for treatment.

The methods thus may entail a first step of providing a sample of tumor cells. The determining step may occur purely in vitro, i.e., without a step interacting on the human or animal body.

According to particular embodiments, the tumor is a skin cancer, e.g., BCC, SCC or melanoma. According to further particular embodiments, the tumor is melanoma.

Increased levels of LINC01212 gene product (i.e., typically lncRNA) are typically increased versus a control. The skilled person is capable of picking the most relevant control. This will typically also depend on the nature of the disease studied, the sample(s) that is/are available, and so on. Suitable controls include, but are not limited to, similar samples from subjects not having a tumor, the average levels in a control group (or control cells, e.g., melanocytes), or a set of clinical data on average LINC01212 gene product levels in the tissue from which the sample is taken. As is evident from the foregoing, the control may be from the same subject, or from one or more different subjects or derived from clinical data. Optionally, the control is matched for, e.g., sex, age, etc.

With "increased" levels of LINC01212 gene product as mentioned herein, it is meant levels that are higher than are normally present. Typically, this can be assessed by comparing to control. According to particular embodiments, increased levels of LINC01212 are levels that are 10%, 20%, 25%, 30%, 40%, 50%, 60%, 70%, 75%, 80%, 90%, 100%, 150%, 200% or even more high than those of the control. According to further particular embodiments, it means that LINC01212 gene product is expressed or present, whereas it normally (or in control) is absent. In other words, in these embodiments, determining the increased expression of LINC01212 gene product is equivalent to detecting the presence of LINC01212 gene product. Typically, in such cases, a control will be included to make sure the detection reaction worked properly. The skilled person will appreciate that the exact levels by which LINC01212 gene product needs to be higher in order to allow a reliable and reproducible diagnosis may depend on the type of sample tested and of which product (lncRNA) the levels are assessed. However, assessing the correlation itself is fairly straightforward.

Instead of looking at increased levels compared to a healthy control, the skilled person will appreciate that the reverse, comparing to a control with disease, can also be done. Thus, if the LINC01212 gene product levels measured in the sample are similar to those of a sample with a tumor (melanoma), or are, e.g., comparable to LINC01212 gene product levels found in a clinical data set of cancer patients, this may be considered equivalent to increased LINC01212 gene product levels compared to a healthy control, and be correlated to an increased suitability of treatment. Of course, LINC01212 gene product levels may be compared to both a negative and a positive control in order to increase accuracy of the diagnosis.

According to specific embodiments, when it is established that the tumor is suitable for treatment, the methods may further comprise a step of administering an inhibitor of functional expression of LINC01212 to the subject in which the tumor is present. This in order to treat the tumor.

Also provided herein are methods of diagnosing the presence of melanoma in a subject, comprising the steps of:

Determining the levels of LINC01212 (or LINC01212 gene product) in a sample of the subject;

Correlating the levels of LINC01212 in the sample with the presence of melanoma.

In such methods, the presence (or increased expression) of LINC01212 is indicative of the presence of melanoma in the subject from whom the sample is taken. Typically, these methods are performed in vitro, although in vivo methods are not necessarily excluded. Determining the levels of LINC01212 will typically be done by determining the levels of LINC01212 RNA in the sample. The same considerations regarding samples and controls apply as described above.

The sample can be a tissue sample (e.g., a skin biopt), but as is shown herein, in melanoma patients, LINC01212 also circulates in the blood. Thus, it can also be detected in blood or serum, and the sample can be a blood sample or a serum sample.

Figure 6:
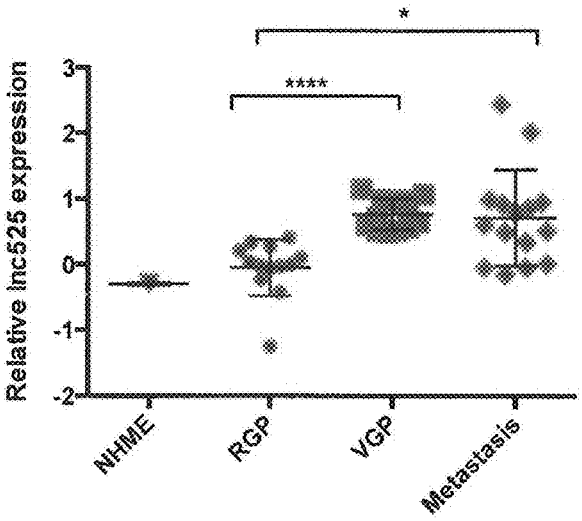
FIG. 6 shows relative LINC01212 expression (normalized with three different reference genes) in normal human melanocytes (NHME) and in RGP (radial growth phase), VGP (vertical growth phase) (isolated by laser capture microdissection) and metastatic human melanoma samples.
Figure 7A:
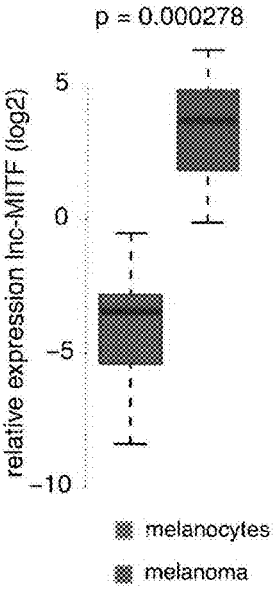
FIG. 7A: Relative expression in melanoma cell lines and primary melanocytes shows increased expression of lncRNA525 in melanoma cells.
Figure 7B:
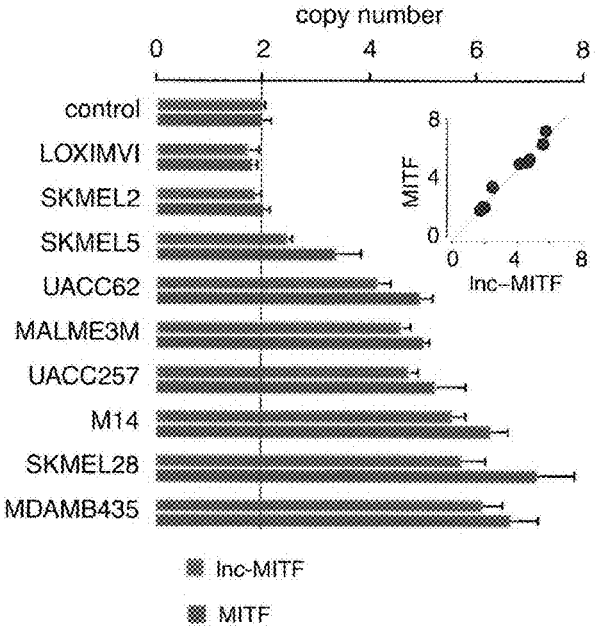
FIG. 7B: High correlation between MITF and LINC01212 (indicated as lnc-MITF) copy number in melanoma cell lines. LINC01212 is co-amplified with MITF explaining, in part, increased LINC01212 expression in melanoma.
Figure 7C:
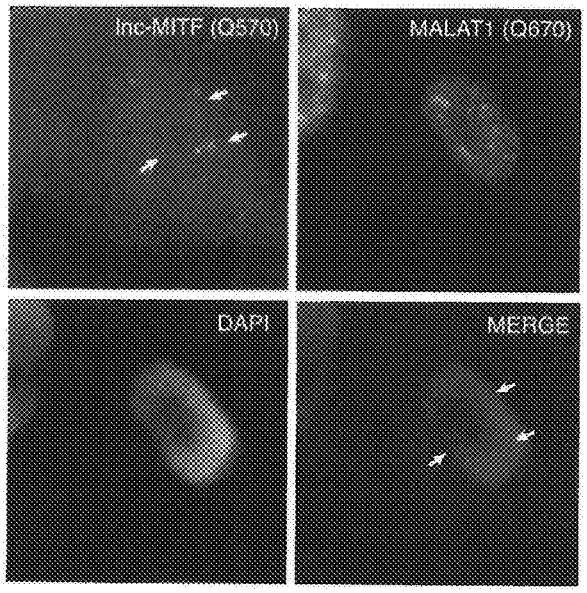
FIG. 7C: Cellular location of LINC01212 transcript in SKMEL28 melanoma cells, visualized by means of RNA-FISH. LINC01212 transcripts are predominantly expressed in the nucleus although several transcripts are detected in the cytoplasm as well, suggesting that this lncRNA might have nuclear and cytoplasmic functions.
Figure 8:
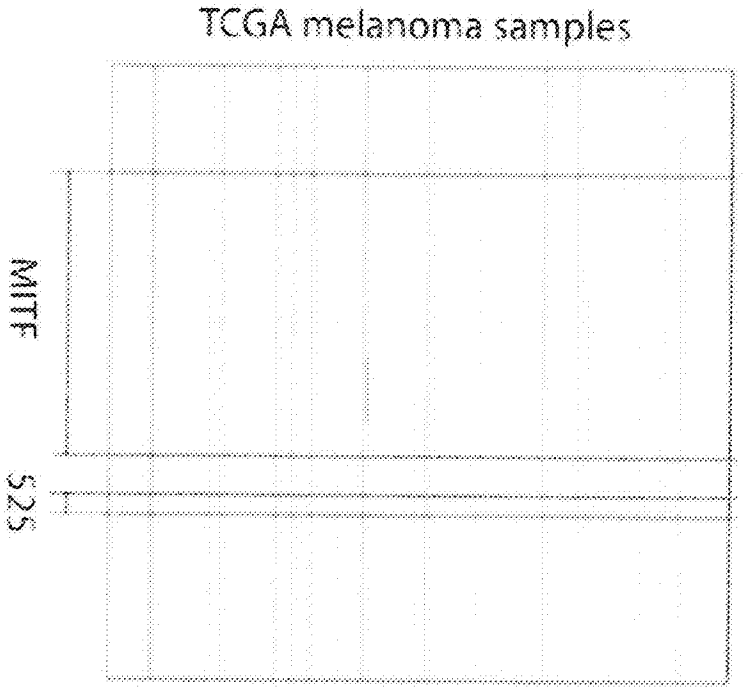
FIG. 8 is a copy number analysis of the MITF and LINC01212 containing genomic region in more than 200 human melanoma patients (TCGA data) indicating that the LINC01212 locus is present in all of the MITF-containing amplicons (no lines: present in two copies; red lines indicate the presence of more than two copies; blue lines indicate deletions, less than two copies).

The levels of LINC01212 RNA vary with different stages of the disease (FIG. 6). Accordingly, in methods that determine the presence of melanoma, a further step may be included that correlates the levels of LINC01212 to disease severity, disease stage (e.g., stage of melanoma), or disease progression.

It is to be understood that although particular embodiments, specific configurations as well as materials and/or molecules, have been discussed herein for cells and methods according to this disclosure, various changes or modifications in form and detail may be made without departing from the scope and spirit of this disclosure. The following examples are provided to better illustrate particular embodiments, and they should not be considered limiting the disclosure. The disclosure is limited only by the claims.

EXAMPLES

Example 1

Identification of a Melanoma-specific lncRNA

Long non-coding RNAs (lncRNAs) are the most abundant class of ncRNA molecules and are emerging as an important regulatory layer of the transcriptome. Currently, expression and function of lncRNAs during human disease and development is largely unexplored. In part, this is due to the fact that few platforms are available that allow sensitive and specific high-throughput lncRNA expression profiling.

1718 MIQE-validated lncRNA RT-qPCR assays were spotted in triplicate on a SmartChip (5184 wells). lncRNA expression is measured by RT-qPCR in 100 nl reactions. Triplicate expression values are combined based on the median Cq, which is insensitive to outliers. lncRNA expression data is normalized using the global mean (Biogazelle's qbase+software).

Expression of 1718 lncRNAs was measured by means of RT-qPCR in 60 cancer cell lines (NCI60 cancer cell line panel, representing nine different tumor entities). This revealed cancer-specific lncRNA expression profiles. Several lncRNAs were identified with a highly specific expression pattern in the nine melanoma cell lines of this panel. Of note, one of these melanoma-specific lncRNAs, ENST00000483525 (aka lncRNA-525), product of the LINC01212 gene, is located immediately downstream of microphthalmia-associated transcription factor (MITF), a lineage-specific oncogene in melanoma (FIG. 1).

Figure 2:
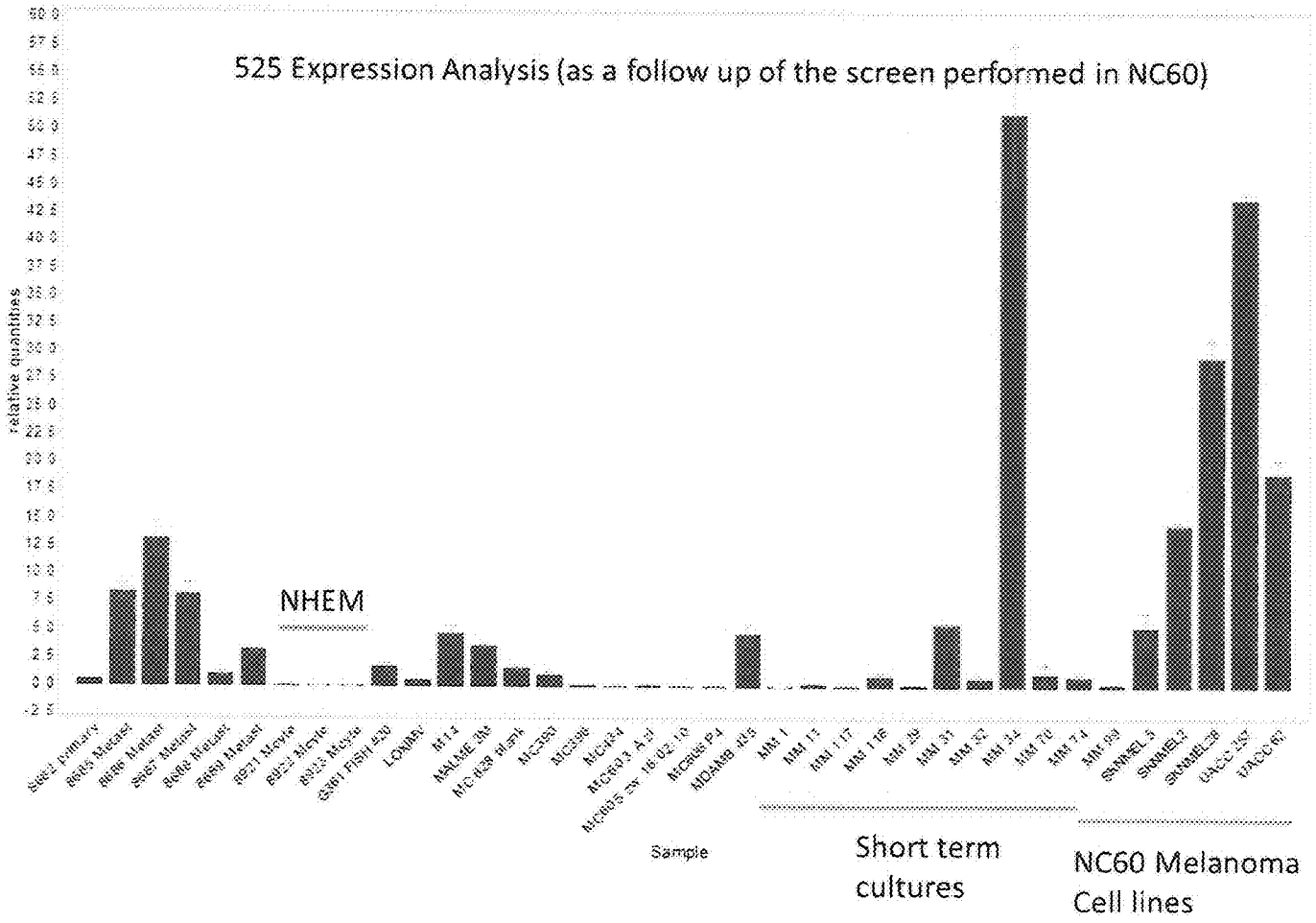
FIG. 2 is the expression analysis of the LINC01212 gene in different cell lines with emphasis on melanoma cell lines and normal human epidermal melanocytes (NHEM).
Figure 3A:
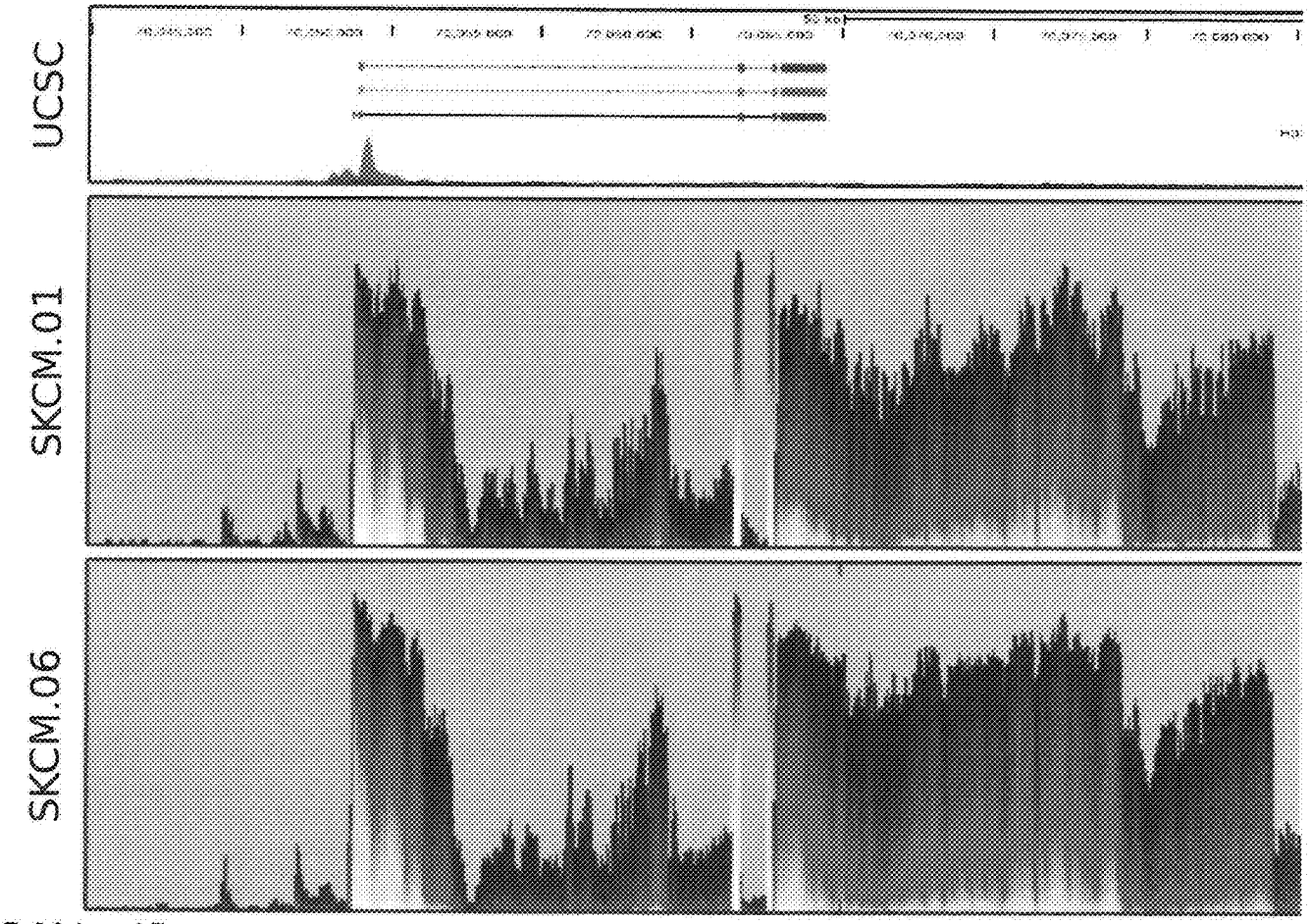
FIGS. 3A-3F are heat maps of the long isoform of LINC01212 expression based on the analysis of RNA-seq data from >200 human melanoma samples from TCGA (SKCM01 non-metastatic versus SKCM06 metastatic samples). The top panel shows that the actual transcript is longer than the UCSC annotated lncRNA-525 transcript. The bottom panel shows that the transcript can be detected in greater than 85% of both metastatic and non-metastatic human melanoma samples.
Figure 3B:
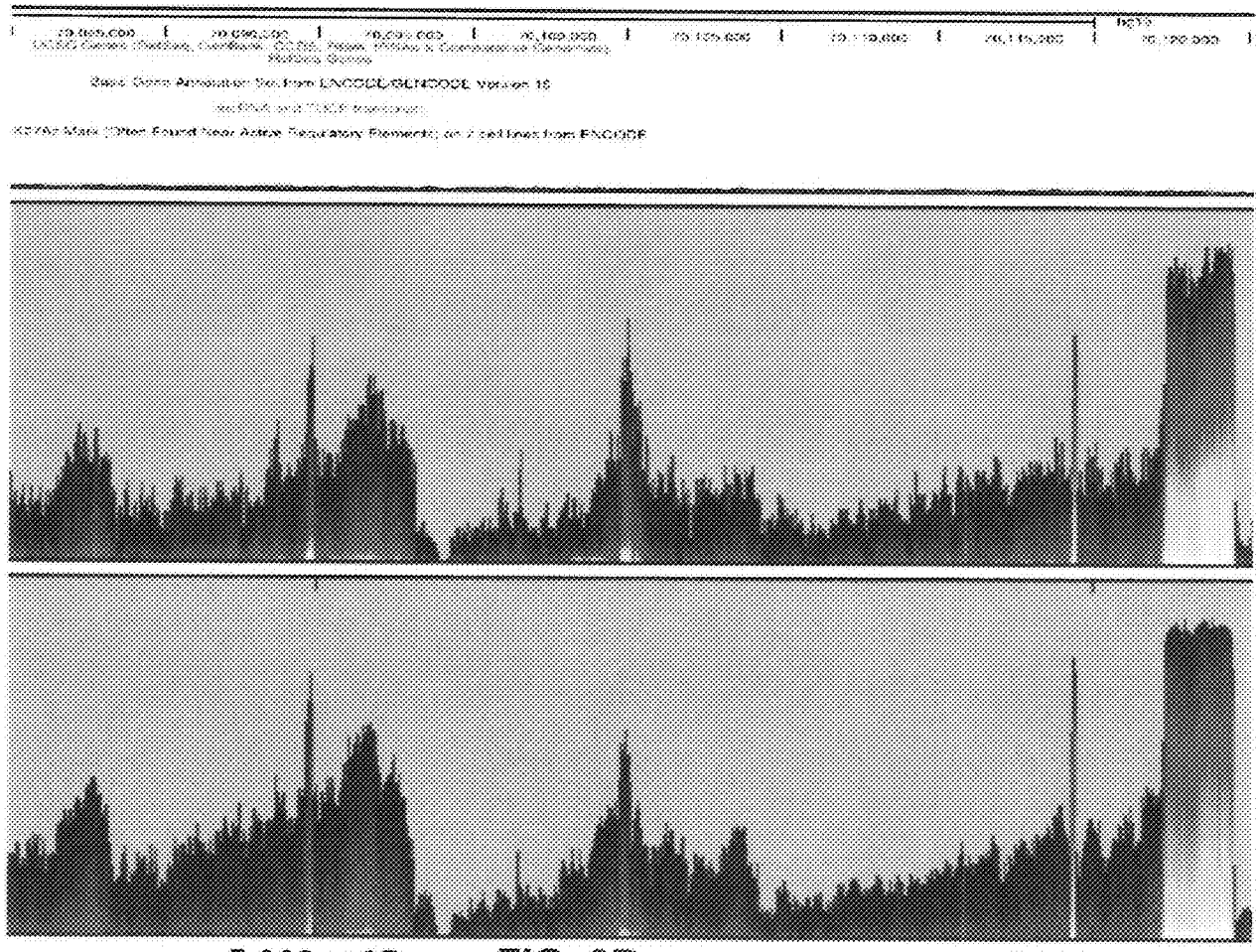
Figure 3C:
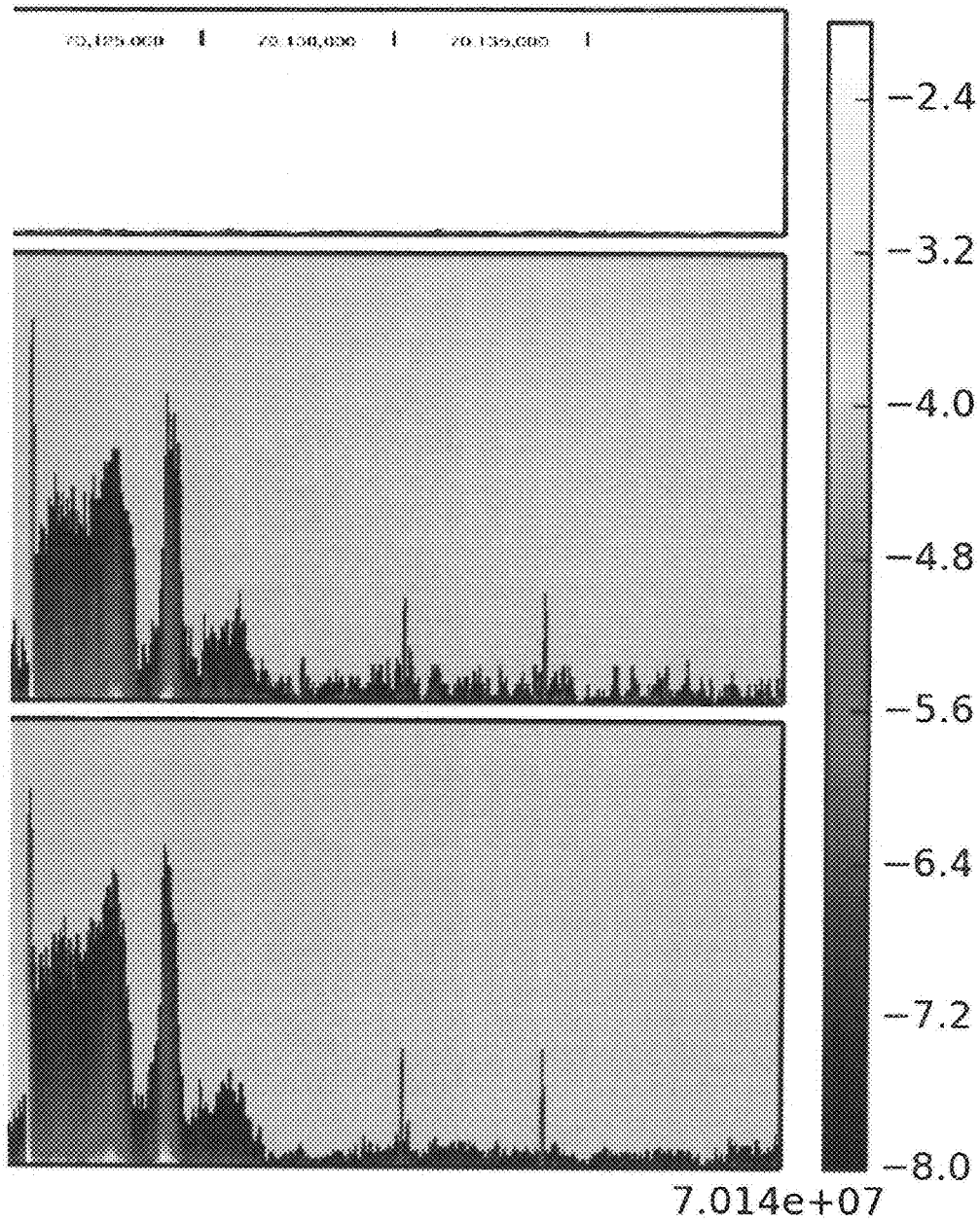
Figure 3D:
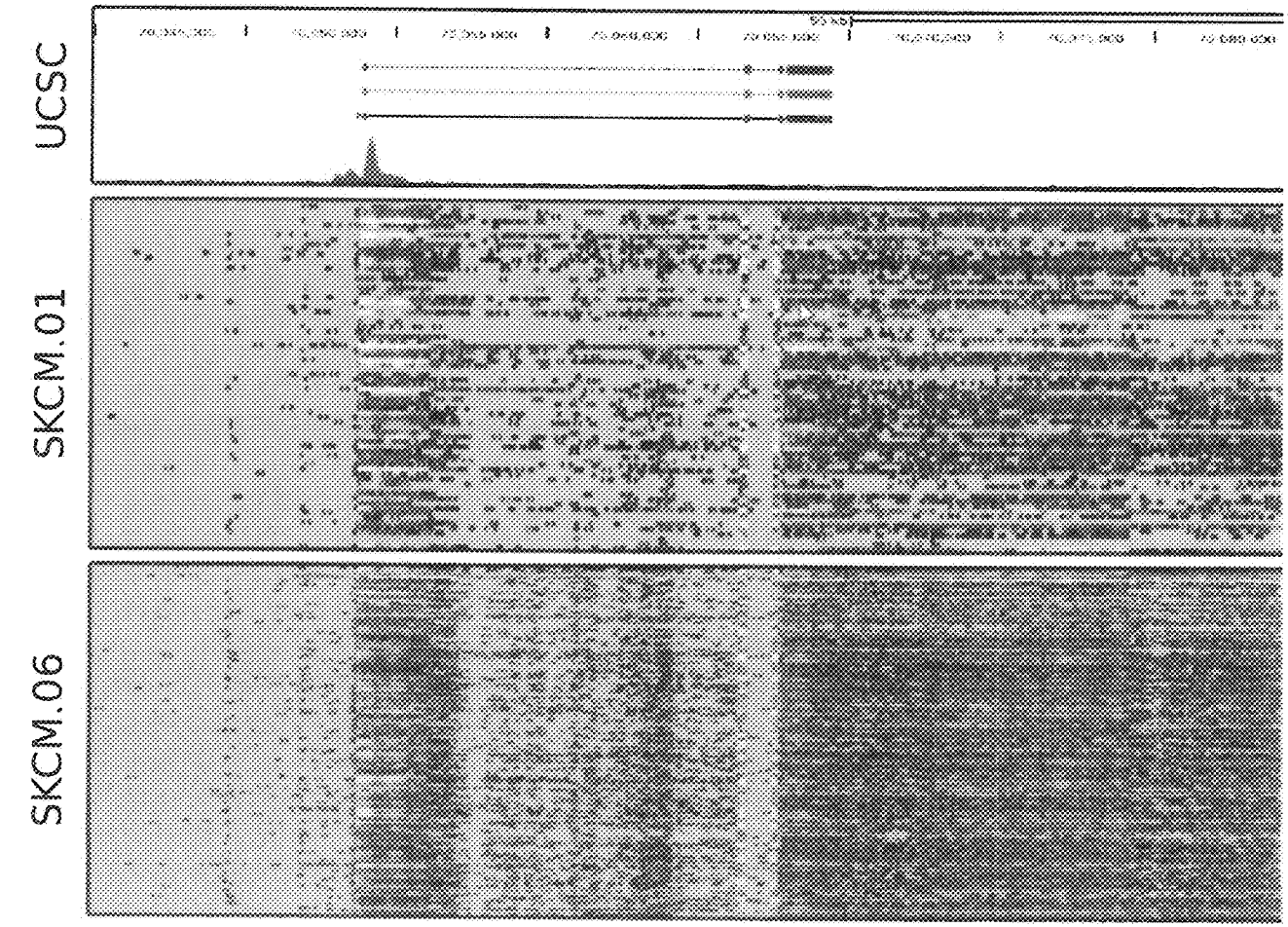
Figure 3E:
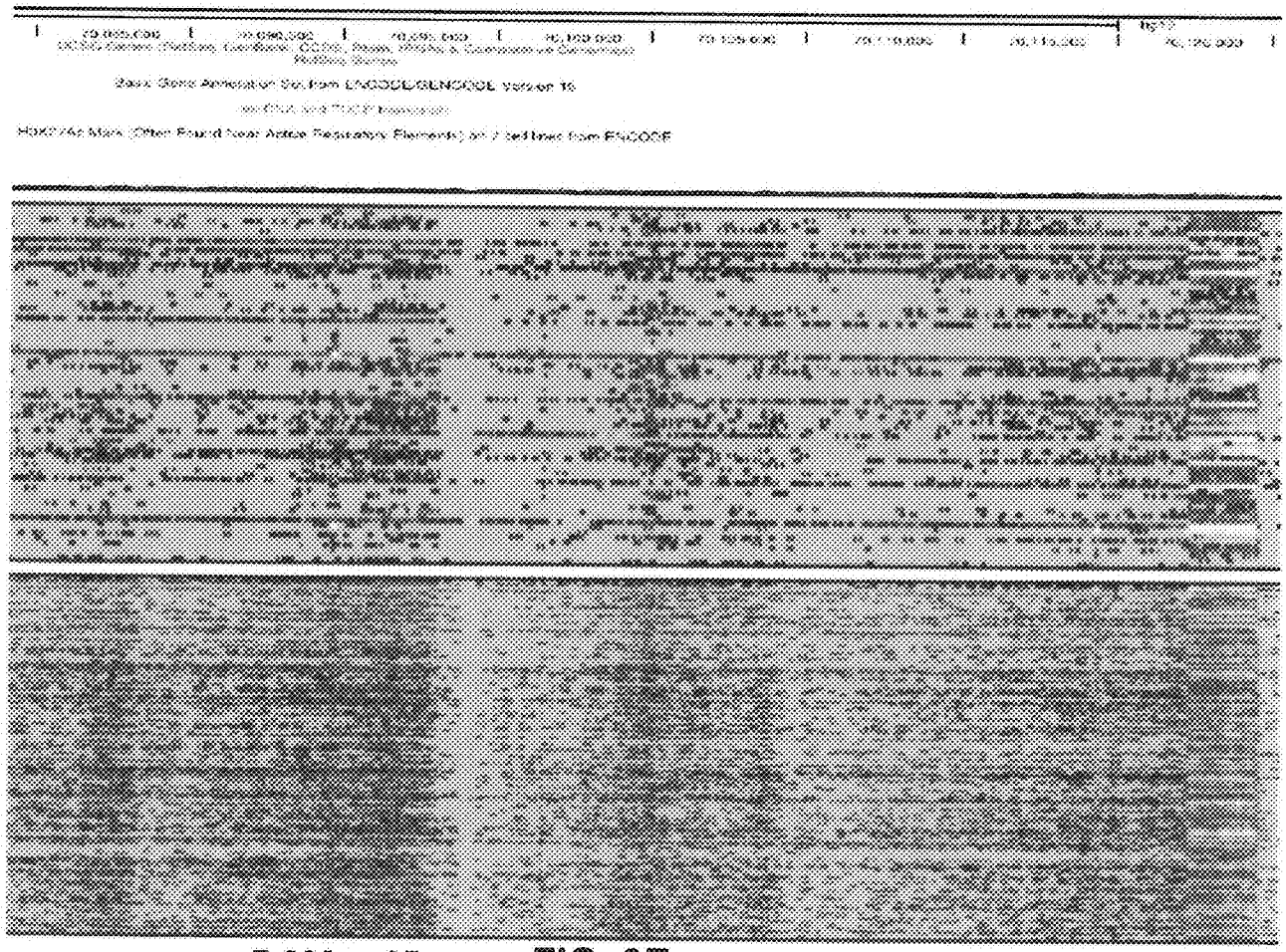
Figure 3F:
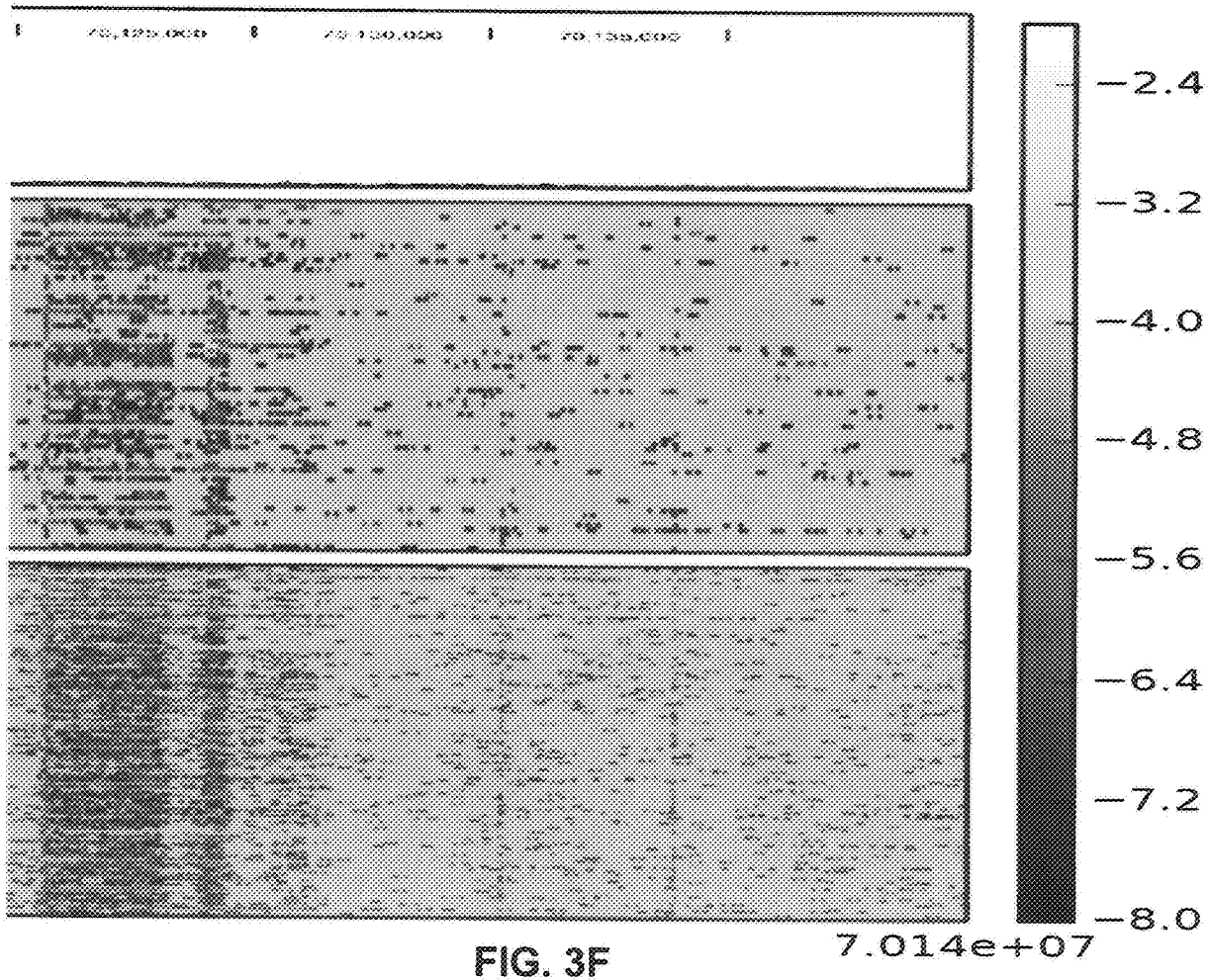
Figure 4:
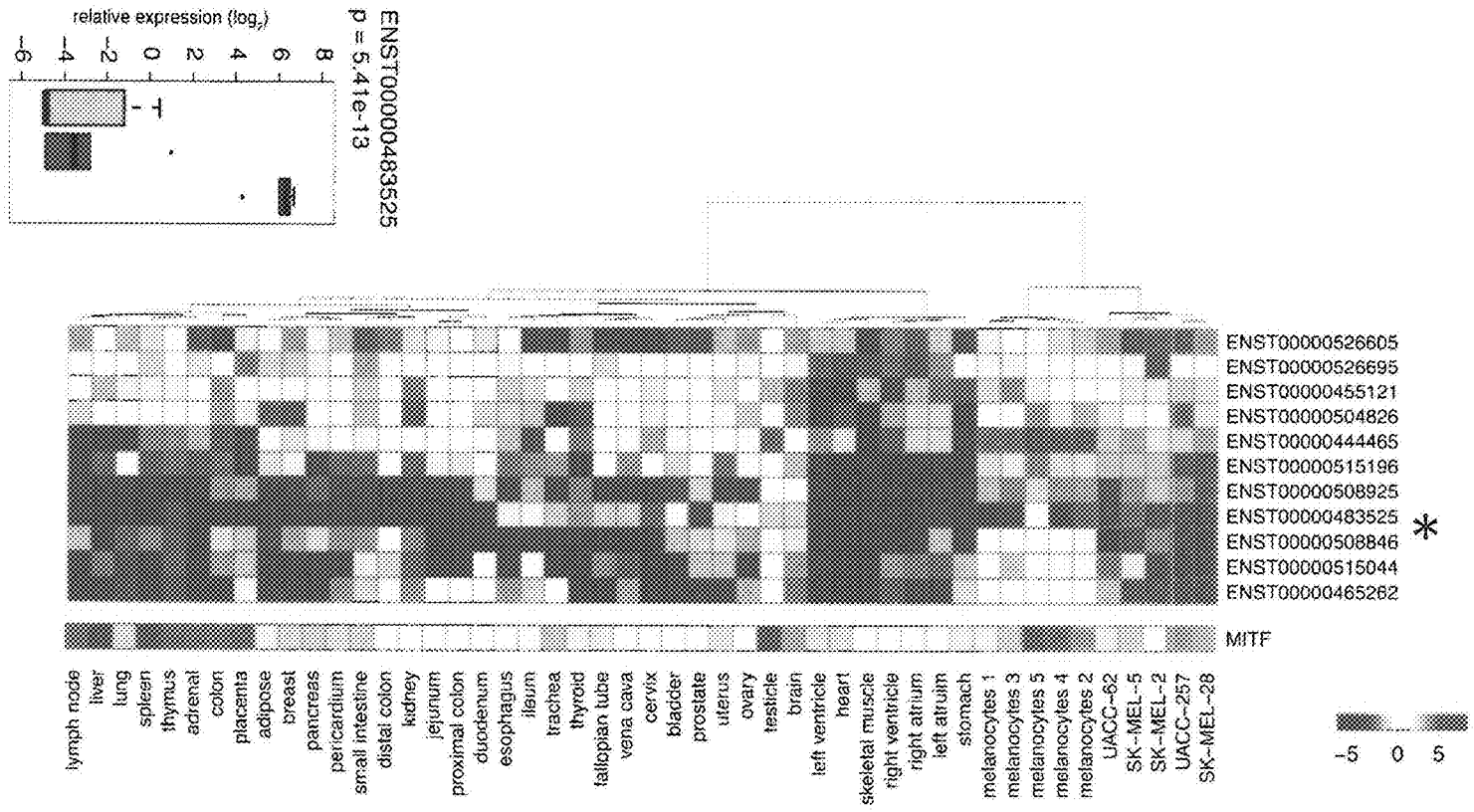
FIG. 4 is a heat map of LINC01212 expression in normal melanocytes, human melanoma cell lines and normal adult tissues (top panel). Relative LINC01212 expression (normalized with three different reference genes) in normal tissues, primary melanocytes and human melanoma cell lines (bottom panel).
Figure 5:
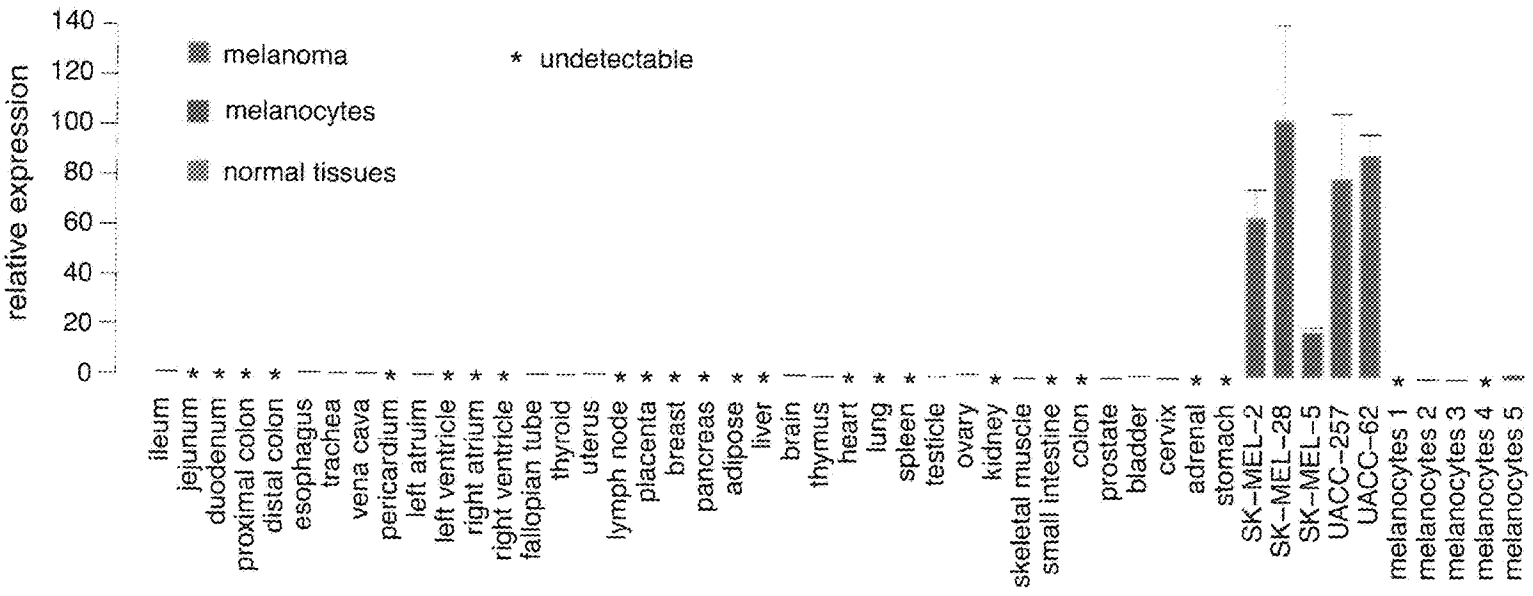
FIG. 5 shows LINC01212 expression in 38 normal human adult tissues, primary melanocytes and melanoma cell lines. Expression data demonstrate the melanoma-specific expression pattern of LINC01212.

When assessing expression of the lncRNA in different cells, it is striking that high expression levels are only observed in short-term melanoma cultures, melanoma cell lines of the NCI60 panel, and metastatic melanomas. In contrast, no significant expression is observed in Normal Human Epidermal Melanocytes (NHEM) (see FIG. 2). Further analysis showed that the lncRNA is specifically expressed in more than 85% of human melanomas (FIGS. 3A-3F) but not in normal human melanocytes or other normal adult tissues (FIGS. 4 and 5), nor in other cancer cell lines (not shown).

While the LINC01212 gene is not expressed in normal human melanocytes (NHEM), its expression is up-regulated very early during melanomagenesis (but is not expressed in benign nevi); its expression is specifically increased during the transition from Radial Growth Phase (RGP) to Vertical Growth Phase, which coincides with the switch from benign (immortalized) to fully transformed melanoma (FIG. 6). It is found overexpressed in some melanomas regardless of stage, from early melanoma lesions (stage I—primary melanomas) to stage IV melanomas (data not shown). This observation raises the possibility that it could serve as a biomarker for early detection of the benign to malignant switch.

Example 2

Mechanisms of Overexpression

To check the cause for this overexpression of the lncRNA, a copy number analysis was performed in nevi, different melanoma cell lines (including NCI60 melanoma cell lines), short-term melanoma cultures and primary melanocytes (NHEM). It could be shown that, in some cases of melanoma, a rare amplification (more precisely, a co-amplification with the MITF locus) may explain the observed overexpression. The LINC01212 gene is located immediately downstream of the MITF locus and is co-amplified with MITF in a fraction of human melanoma. Gene amplification of the LINC01212 locus can, therefore, explain, in part, its up-regulation in melanoma (FIGS. 7A-7C and 8).

Other epigenetic mechanisms are likely to contribute to LINC01212 up-regulation in melanoma. Evidence has been obtained that the LINC01212 promoter is methylated in NHME and non-melanoma cell lines and is de-methylated in the majority of short-term melanoma cultures analyzed, pointing to another mechanism of LINC01212 expression in melanoma. Experiments aimed at understanding the mechanisms that contribute to demethylation of the LINC01212 promoter during melanomagenesis are ongoing.

Figure 9A:
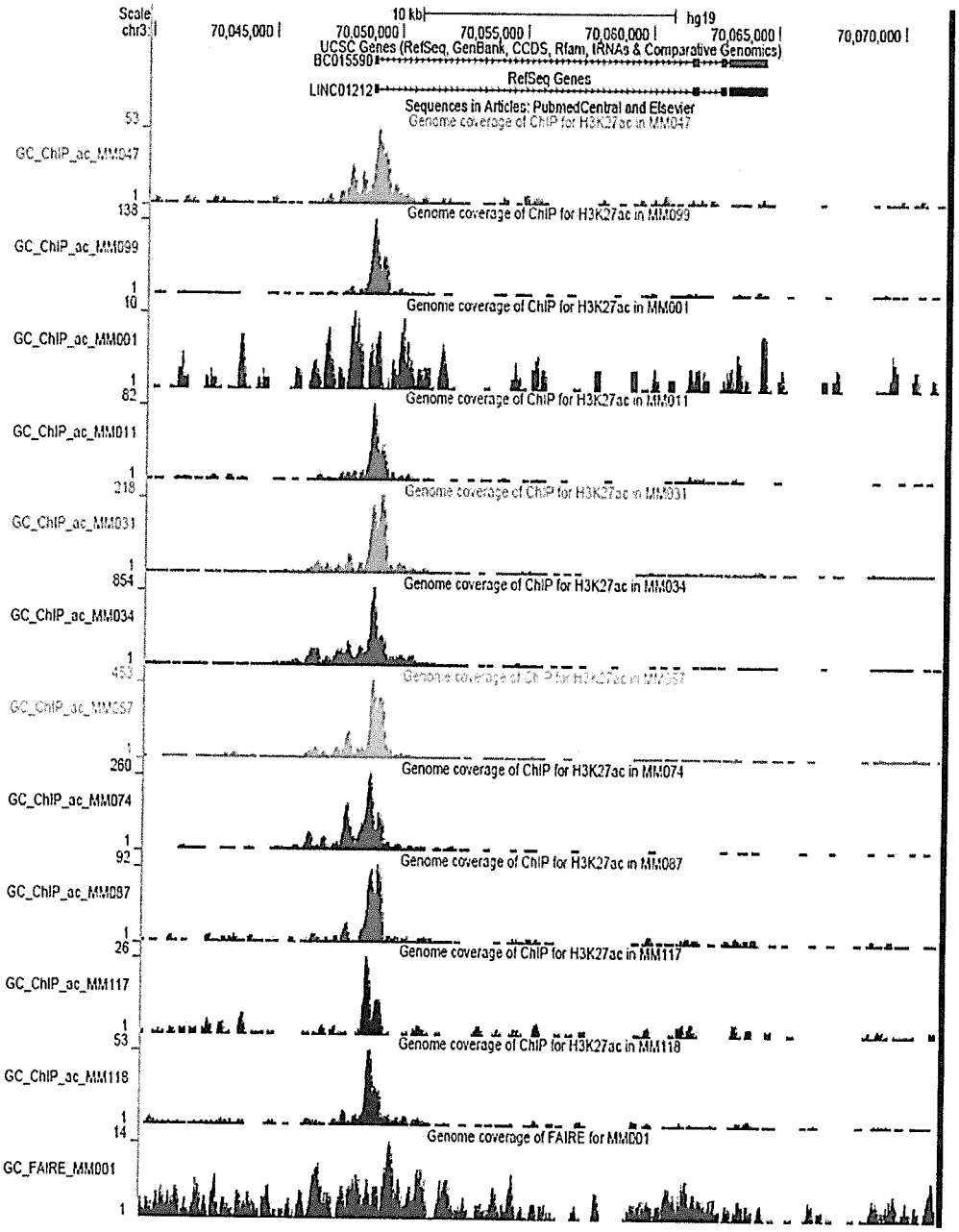
FIGS. 9A-9C show LINC01212 promoter activity as assessed by measuring the H3K27 acetylation landscape. A readily detectable peak is present upstream of the LINC01212 gene indicating that the LINC01212 promoter is active/ON in all but one (MM001) of the melanoma lines analyzed.
Figure 9B:
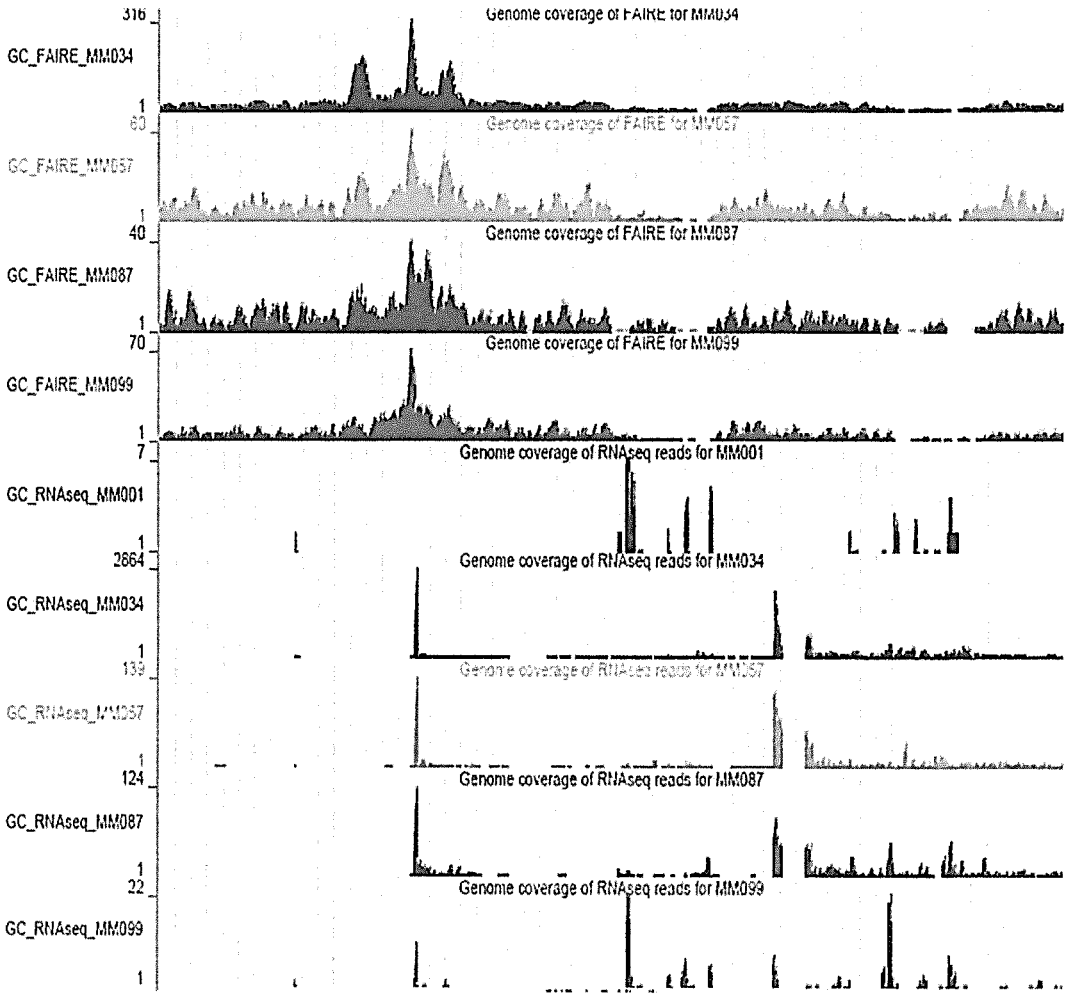
Figure 9C:
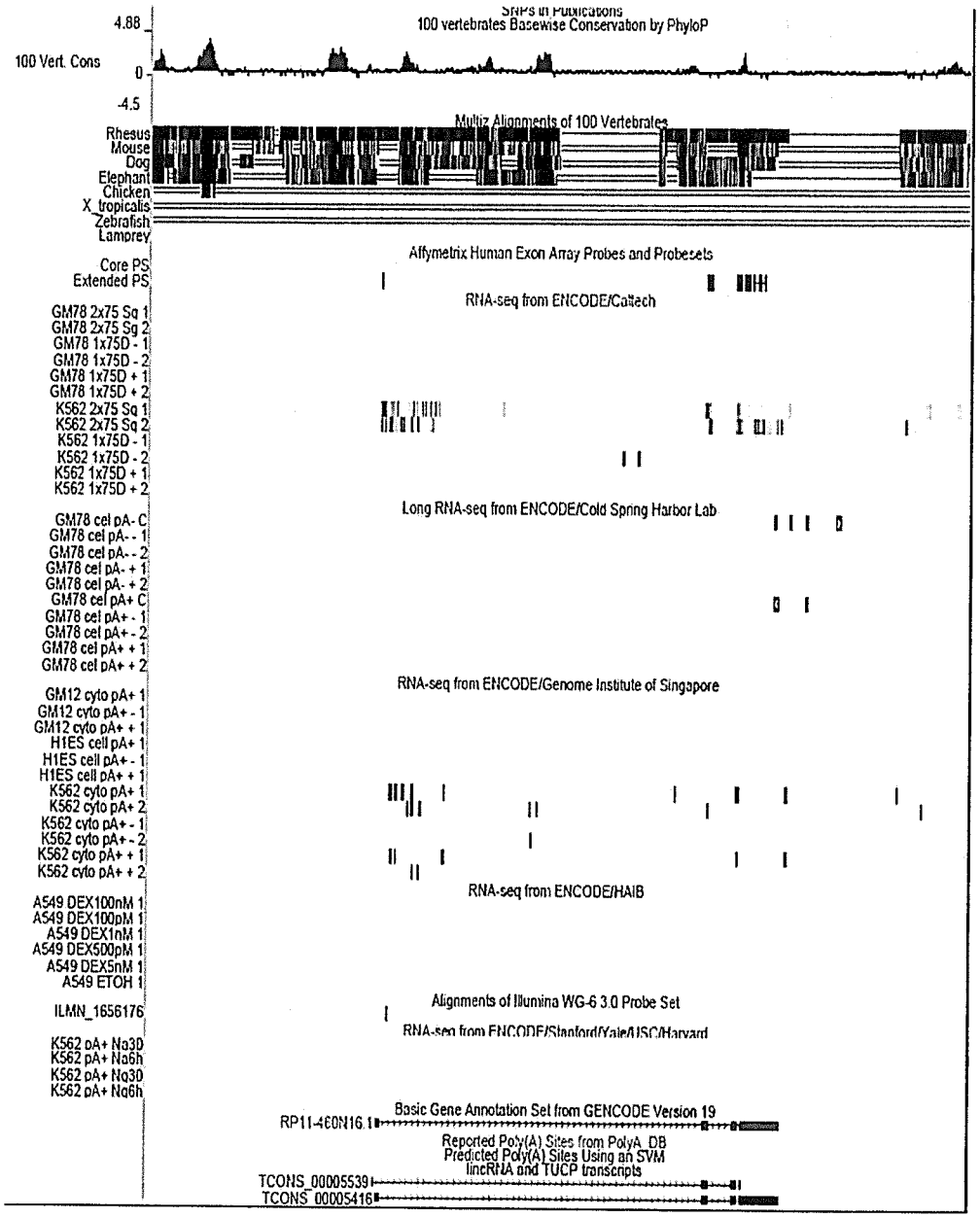

Consistent with the above evidence of increased promoter activity of the LINC01212 gene by demethylation, H3K27 Acetylation ChIP-seq experiments (FIGS. 9A-9C) and FAIRE-seq on a series of short-term culture melanoma lines corroborated the increased promoter activity.

Example 3

Inhibition of the LINC01212 Gene Product Induces Apoptosis Specifically in Melanoma Cells To assess the functional relevance of the observed overexpression of the LINC01212-encoded lncRNA, its expression was inhibited using gapmers. LNA gapmers are potent antisense oligonucleotides used for highly efficient inhibition of mRNA and lncRNA function. Two different gapmers were designed to target the lncRNA. The SK-MEL28 melanoma cell line was chosen as a test cell line, since it is part of the NCI60 panel, and shows high expression of the LINC01212-encoded lncRNA (as a result of a copy number gain).

Figure 10:
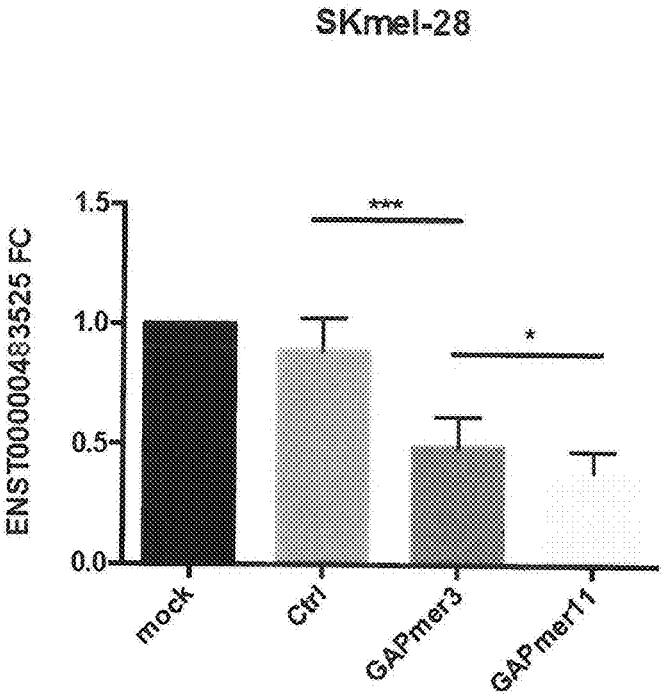
FIG. 10 is an expression analysis of LINC01212 in the SK-MEL28 melanoma cell line transfected with different gapmers (scrambled or directed against the LINC01212 long transcript).

The gapmers effectively succeeded in reducing lncRNA expression in these cells, whereas a control scrambled gapmer had no effect (FIG. 10).

Figure 11:
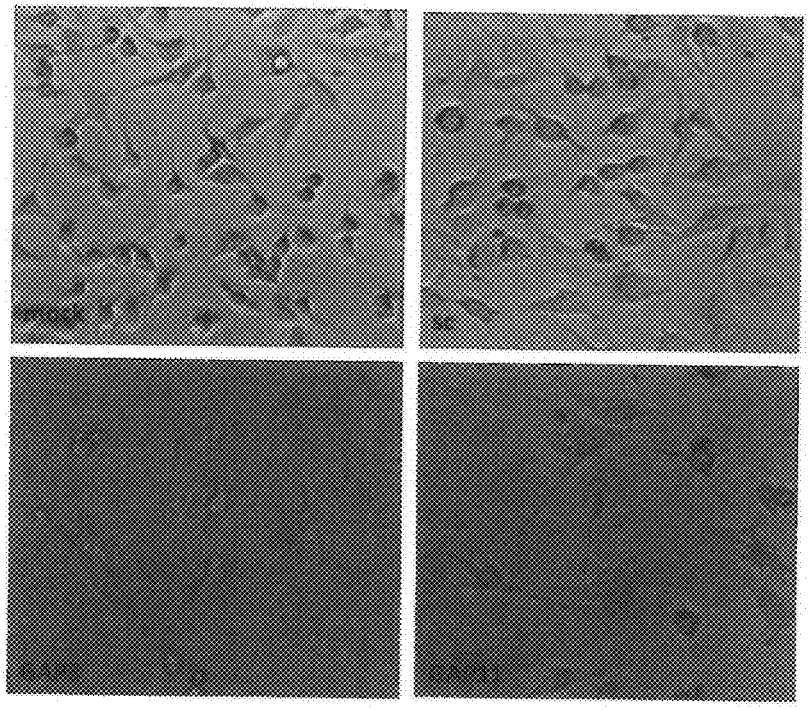
FIG. 11 shows SK-MEL28 melanoma cell lines treated with the lncRNA inhibitors of FIG. 10, showing cell death.
Figure 12:
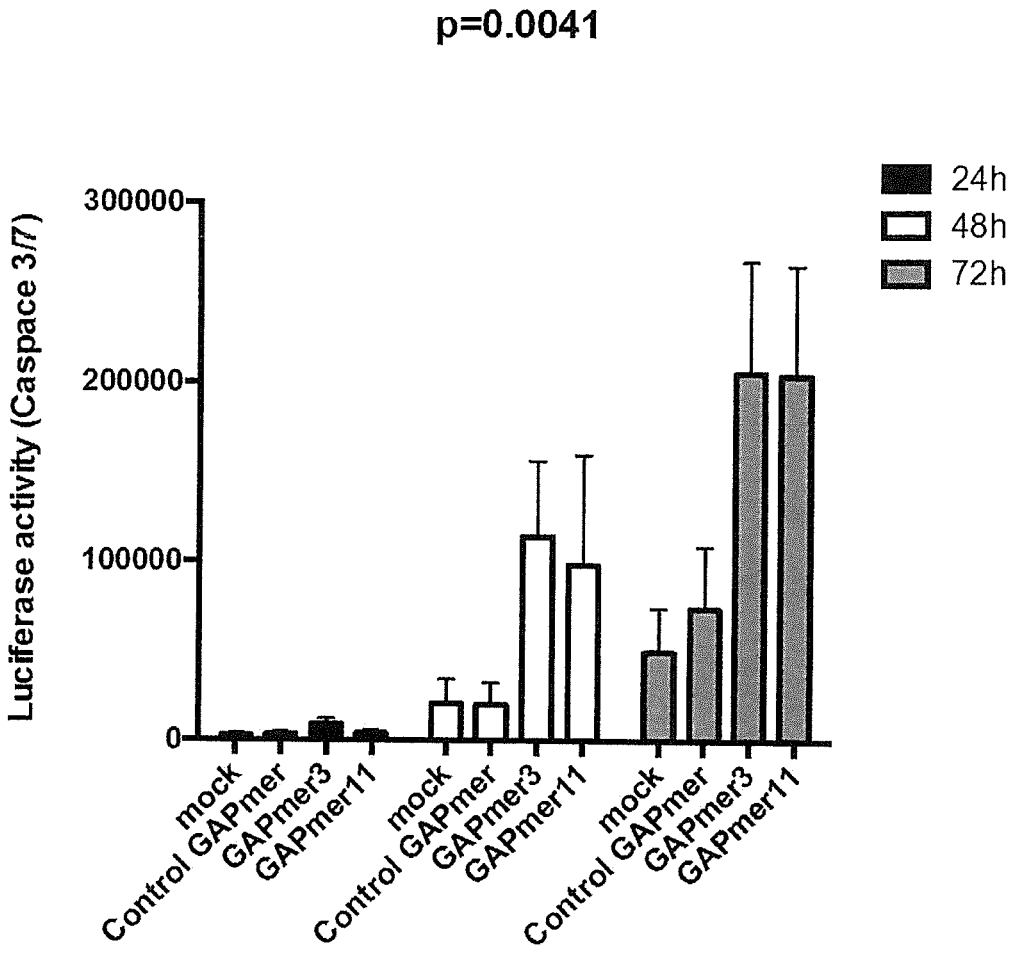
FIG. 12 shows gapmer inhibition in SK-MEL 28, BRAF V600E, P53 mutant. By measuring caspase 3/7 activity with a luciferase reporter, it could be confirmed that knock-down of the LINC01212-encoded lncRNA in SK-MEL28 melanoma cells resulted in a significant induction of apoptosis.

Remarkably, a lot of the cells treated with the lncRNA inhibitors died (FIG. 11). By measuring caspase 3/7 activity with a luciferase reporter, it could be confirmed that knockdown of the LINC01212-encoded lncRNA in SK-MEL28 melanoma cells resulted in a significant induction of apoptosis (FIG. 12).

Figure 13:
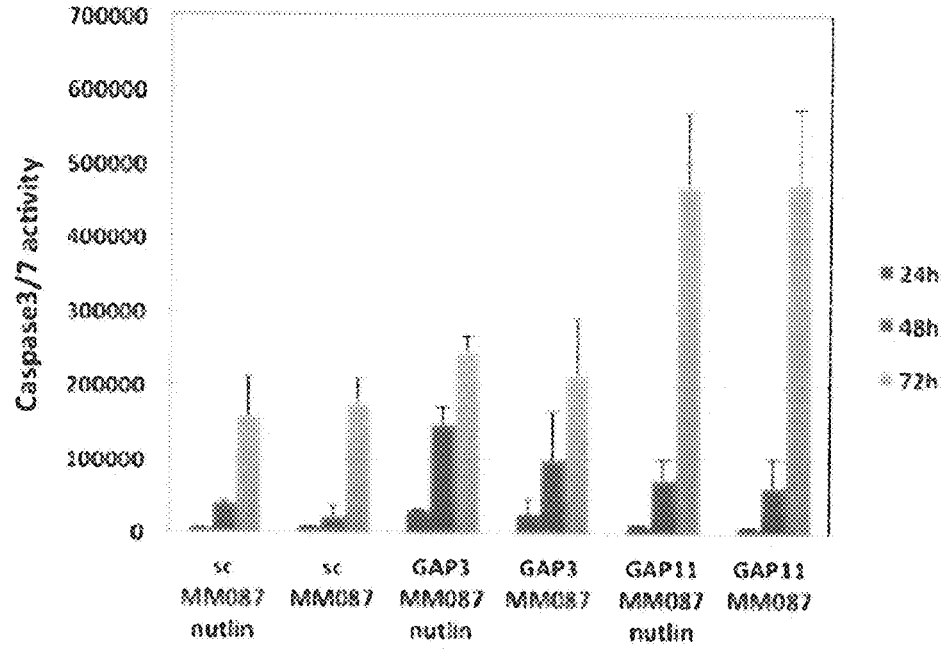
FIG. 13 charts gapmer inhibition in MM034 (BRAFV600E, P53 WT) (lower panel) and MM087 (BRAF WT, NRAS WT, P53 Mutant) (top panel) cells.
Figure 13:
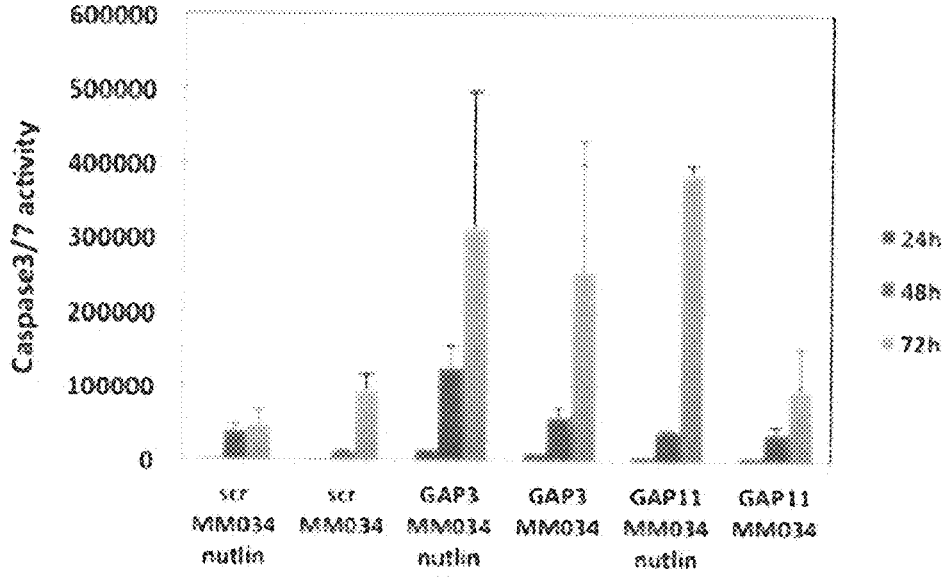
Figure 14A:
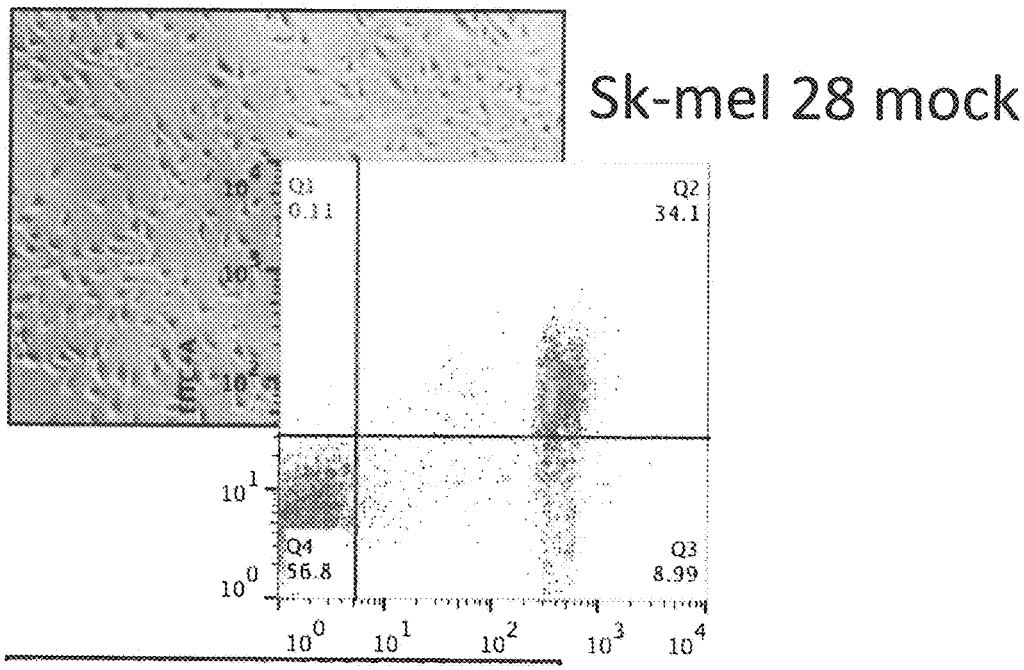
FIGS. 14A-14C show the SK-mel 28 human melanoma cell line was transfected with si-scramble (sc) or siRNA-targeting LINC01212 (and particularly its long transcript) and with gapmer-scramble (sc) or gapmer 3 and 11 (GAP3 and GAP11). Apoptosis was measured using an Annexin-5/PI assay by FACS 48 hours after transfection. Representative pictures of the cells are shown.
Figure 14A:
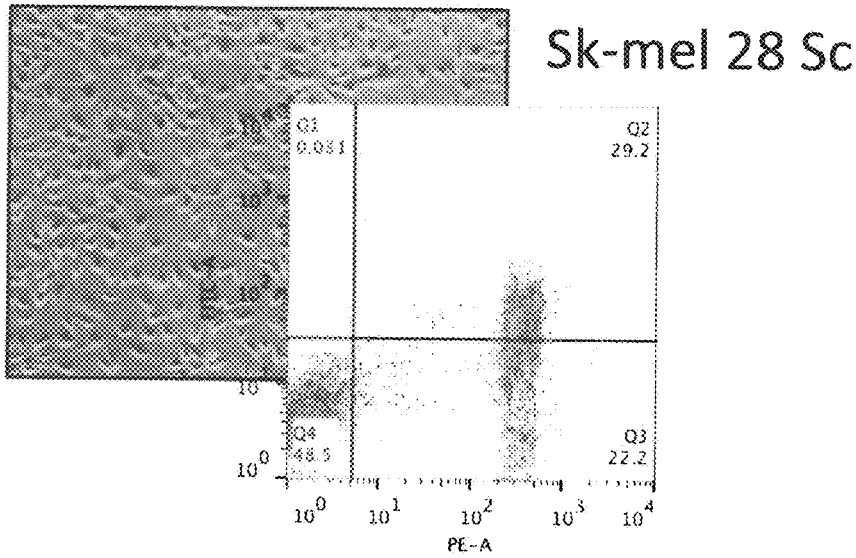
Figure 14B:
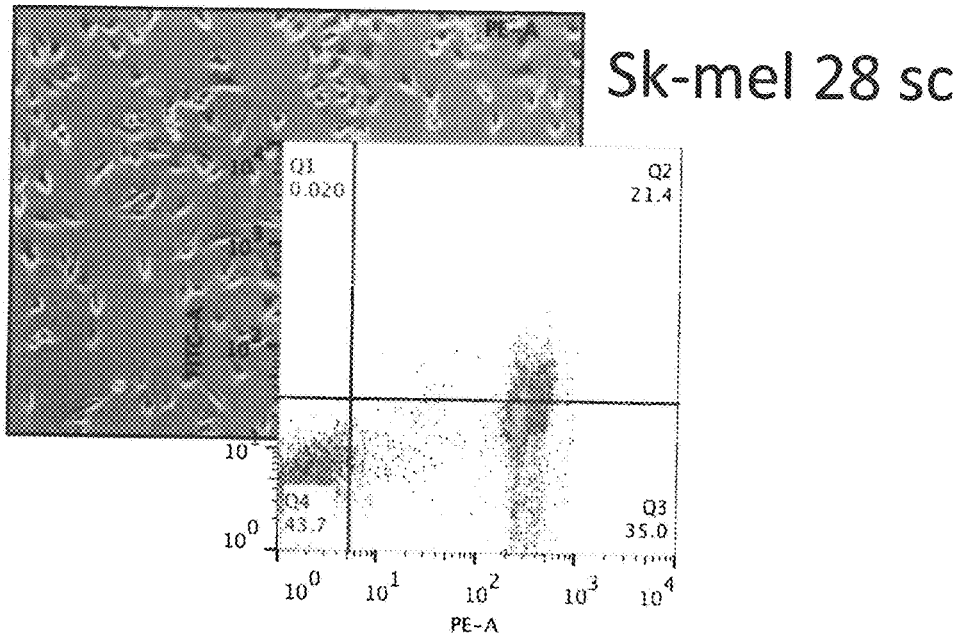
Figure 14B:
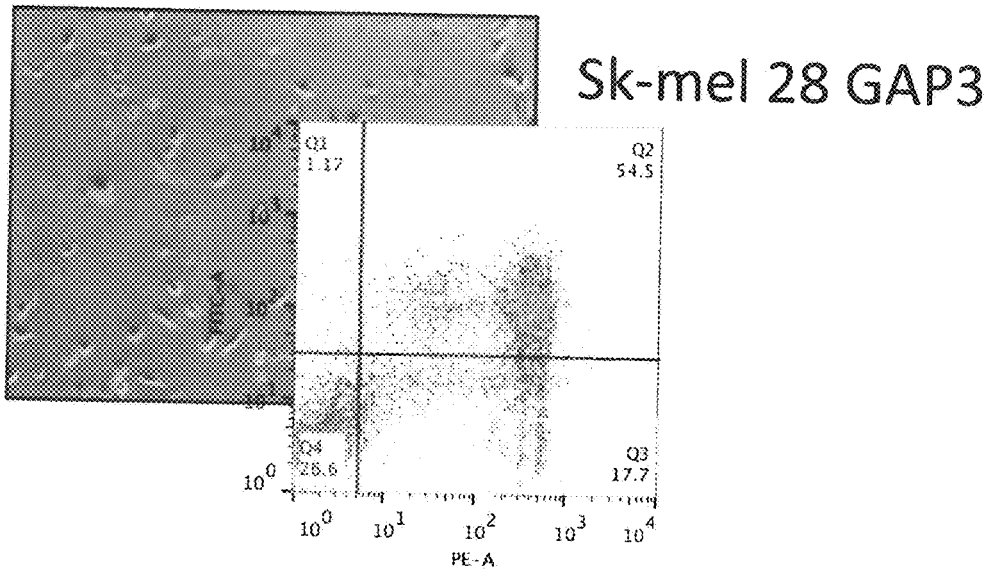
Figure 14C:
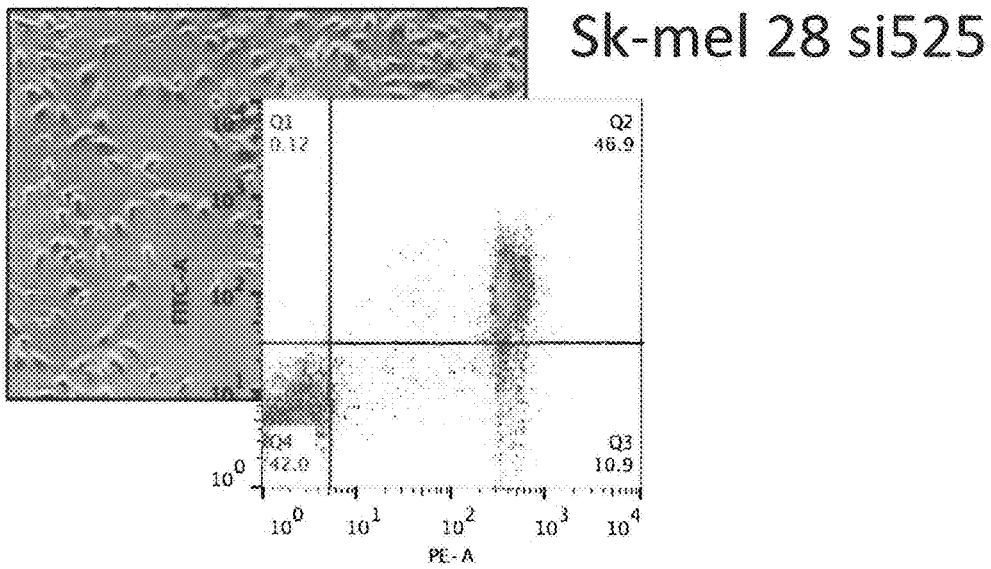
Figure 14C:
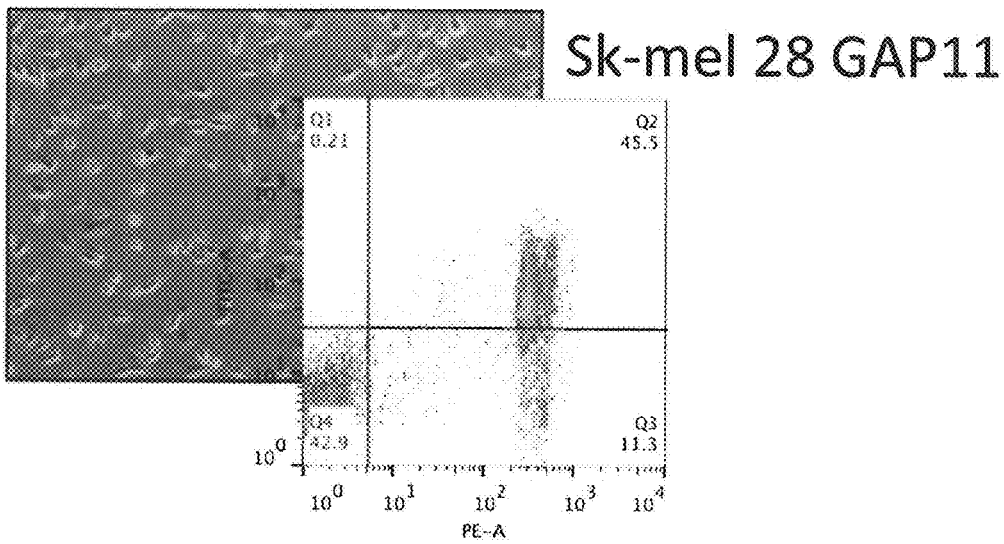

These findings were further validated in two additional melanoma short-term culture systems with differential TP53 status (i.e., wild-type and mutant). Apoptosis induction was observed with both gapmers in both short-term cultures suggesting that the observed phenotype is independent of TP53 status, but also independent of BRAF status (FIG. 13). To our knowledge, this is the first inhibitor that can achieve this.

Thus, strikingly, knocking down this lncRNA, using siRNA or LNA-antisense oligonucleotides, invariably leads to dramatic apoptotic cell death (FIGS. 11 and 14A-14C), irrespective of the BRAF, NRAS (or TP53) status.

Similar results were obtained using melanoma lines with different genetic backgrounds such as, for instance, MM057 (NRAS Q61L) or MM087 (TP53 mutation). Cells that do not express LINC01212, such as NHME, HCT116, and MM001, were not affected by these treatments.

Figure 15A:
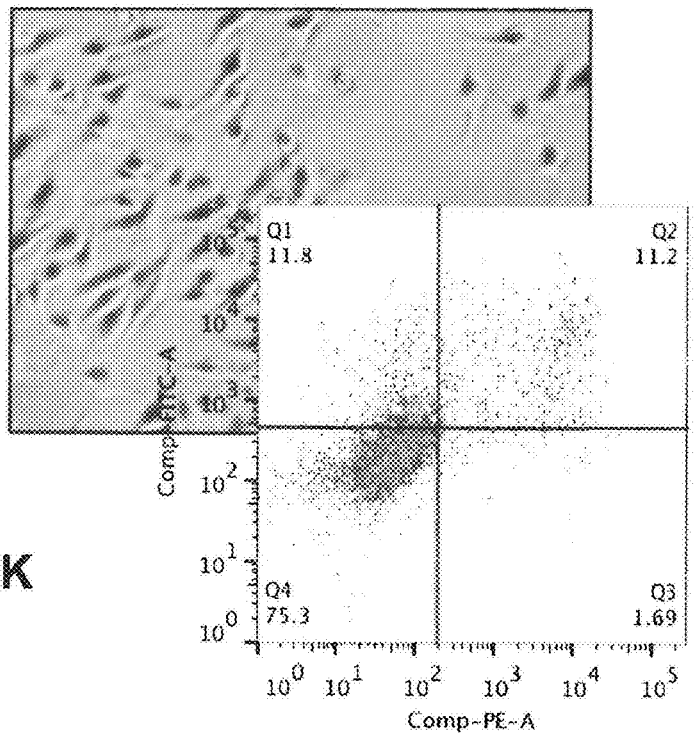
FIGS. 15A and 15B show a stable SK-MEL28 human melanoma cell line engineered to express exogenous LINC01212 was transfected with gapmer-scramble (sc) or 11 (GAP11). Apoptosis was measured using an Annexin-5/PI assay by FACS 48 hours after transfection. Representative pictures of the cells are shown.
Figure 15A:
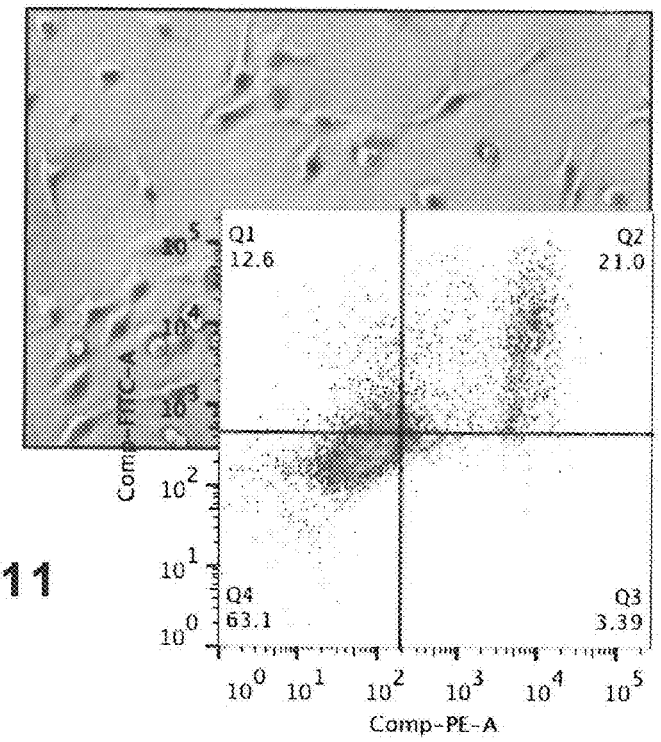
Figure 15B:
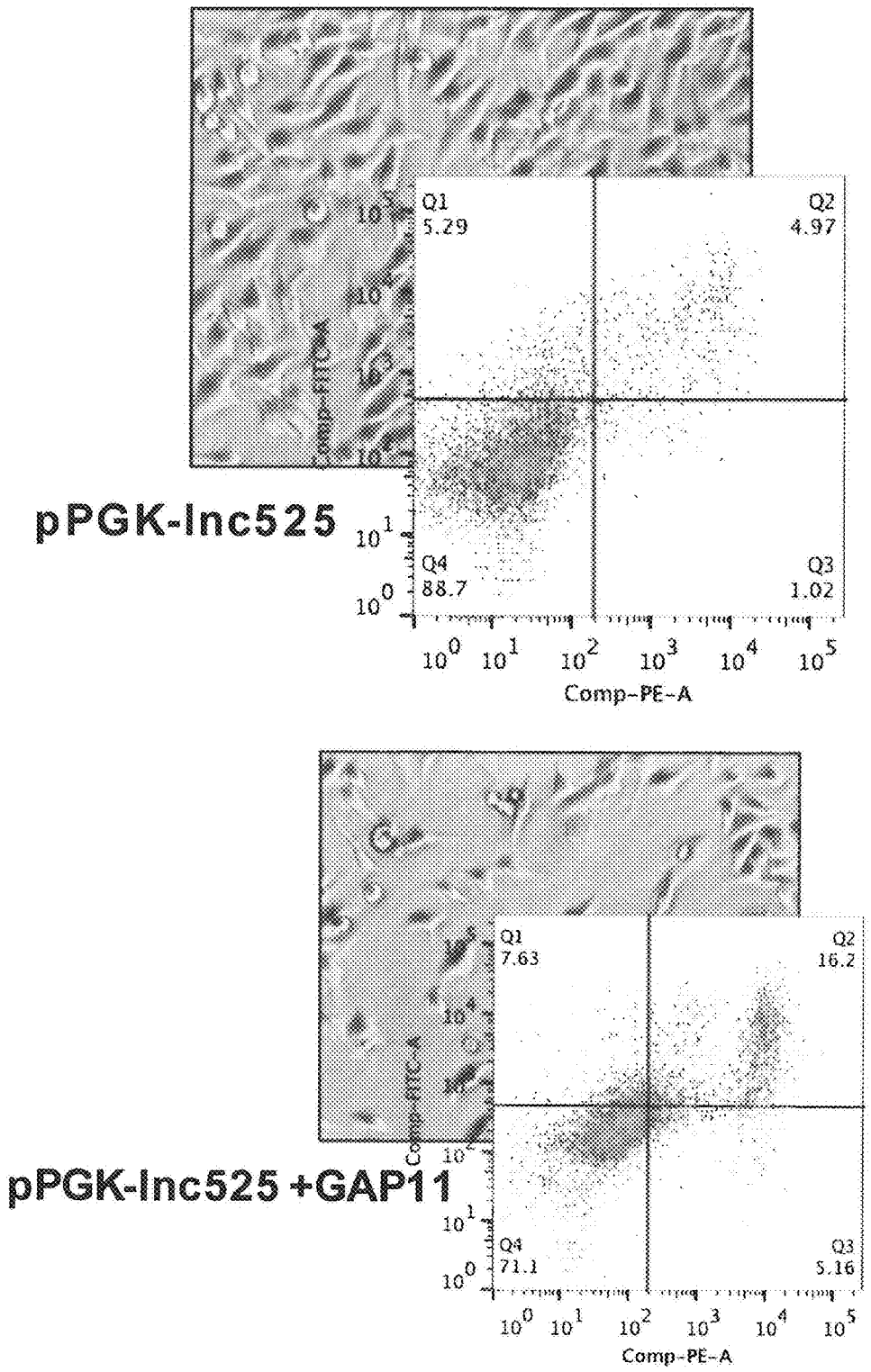

Importantly, overexpression of the annotated long LINC01212 transcript in NMHE and the melanoma SK-MEL28 cells resulted in an increase in cell proliferation and decrease in the basal level of apoptotic cell death (data not shown). Enforced expression of this transcript also rescues at least partly the increase in apoptosis observed upon LINC01212 KD with Gapmer 11 (FIGS. 15A and 15B). Given the FISH analysis indicated that exogenous LINC01212 was mainly localized to the cytoplasm (FIG. 7C), these preliminary data indicate that LINC01212 functions (to protect melanoma cells from apoptosis) at least partly by acting in trans in the cytoplasm.

Figure 16:
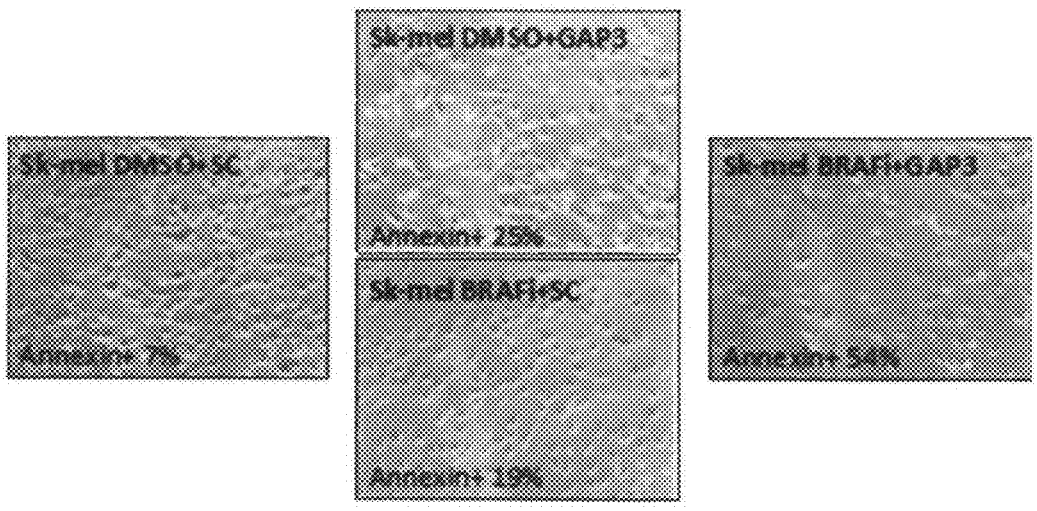
FIG. 16 shows a BRAFV600E human melanoma cell line was transfected with gapmer-scramble (sc) or gapmer 3 (GAP3) and either treated with vehicle (DMSO) or a BRAFV600E-inhibitor. Apoptosis was measured by quantification of Annexin-5-positive cells by FACS 24 hours after exposure to the BRAFV600E-inhibitor (and 48 hours after transfection). Representative pictures of the cells are shown.
Figure 17A:
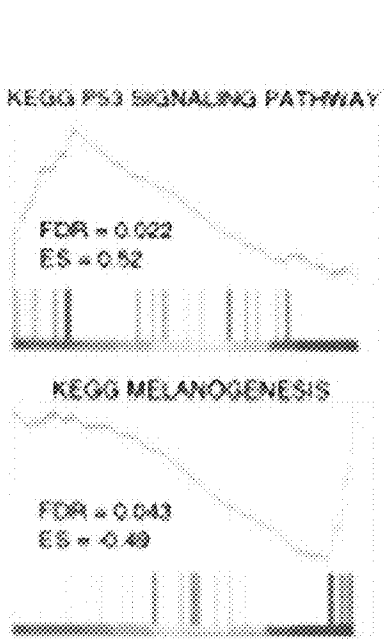
FIGS. 17A and 17B chart full-genome transcriptome gene expression analysis of SKMEL28 cells treated with the different gapmers.
Figure 17B:
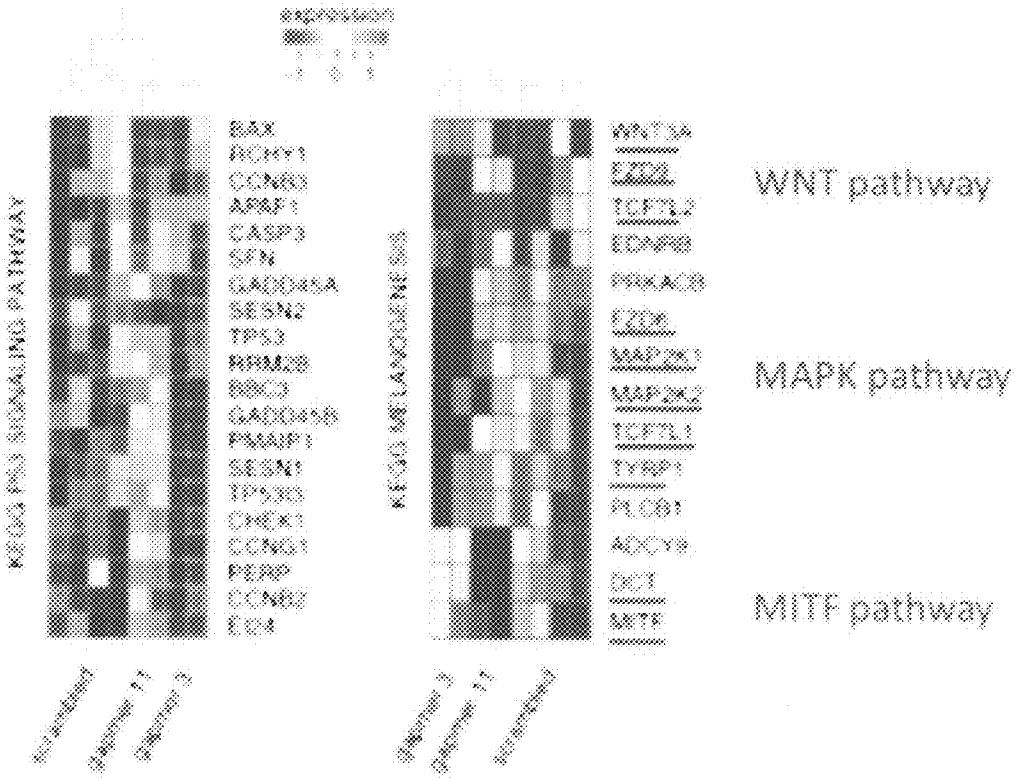
Figure 18:
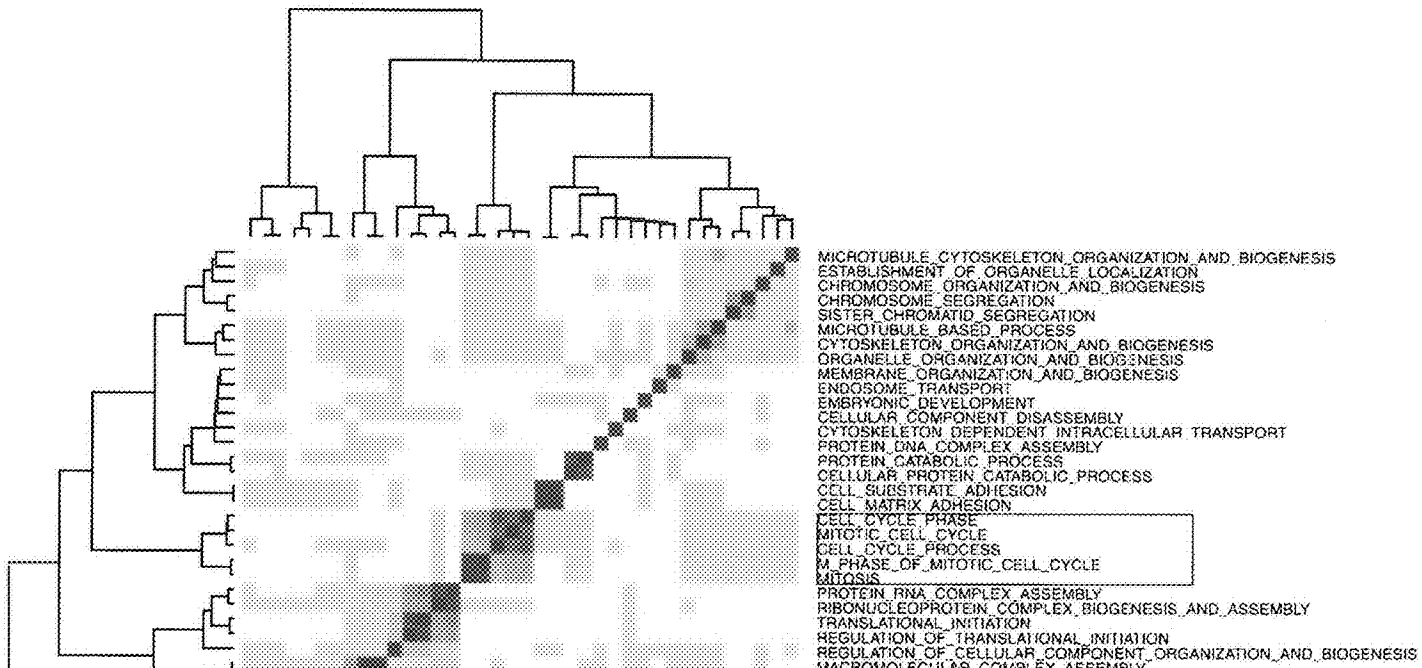
FIG. 18 charts pathways significantly down-regulated upon LINC01212 knock-down in MM034 short-term melanoma cultures. Pathways are identified by means of whole genome mRNA expression profiling upon LINC01212 knock-down and gene set enrichment analysis (GSEA). Pathways are clustered based on pathway overlap. In MM034 cells, LINC01212 knock-down results in a decreased cell cycle activity as evidenced by multiple cell cycle gene sets.
Figure 19A:
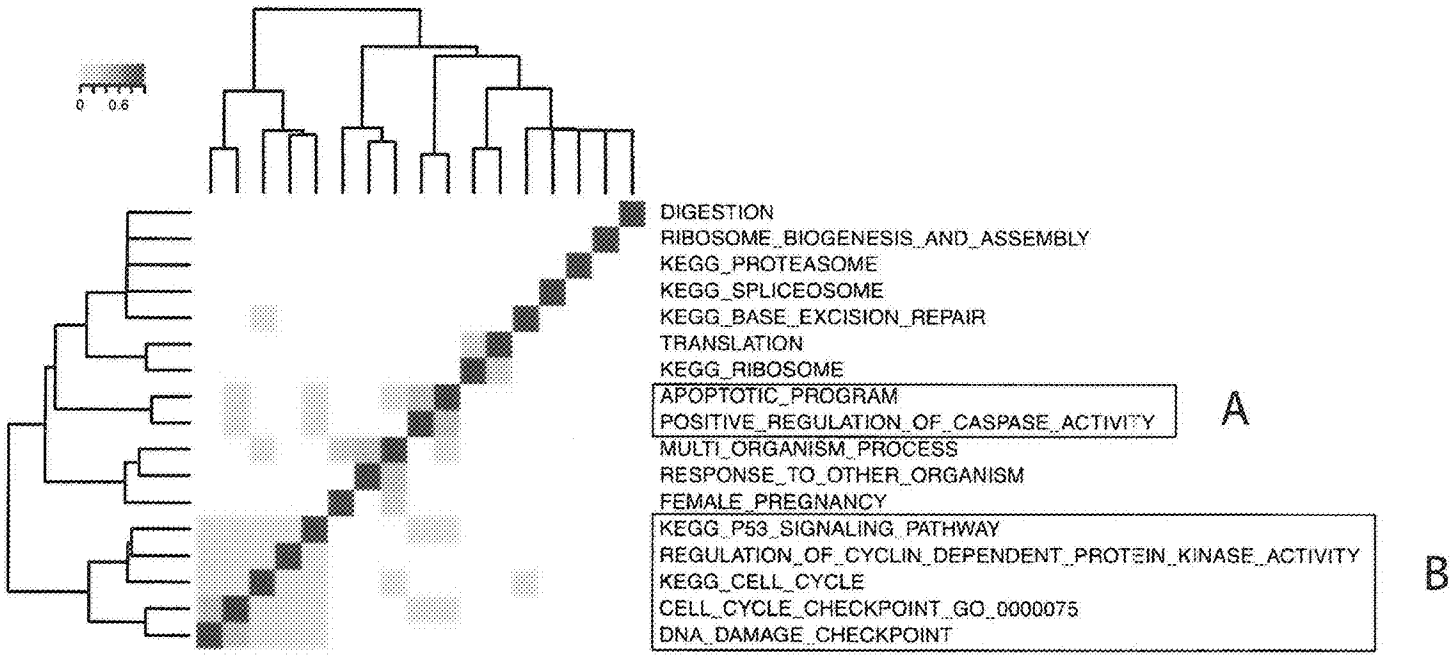
FIGS. 19A and 19B chart pathways significantly up-regulated (top) and down-regulated (bottom) upon lncRNA525 knock-down in SKMEL28 melanoma cells. Pathways are identified by means of whole genome mRNA expression profiling upon LINC01212 knock-down and gene set enrichment analysis (GSEA). Pathways are clustered based on pathway overlap. In SKMEL28 cells, LINC01212 knock-down results in induction of apoptotic and TP53 pathway genes and repression of MAPK and WNT signaling.
Figure 19B:
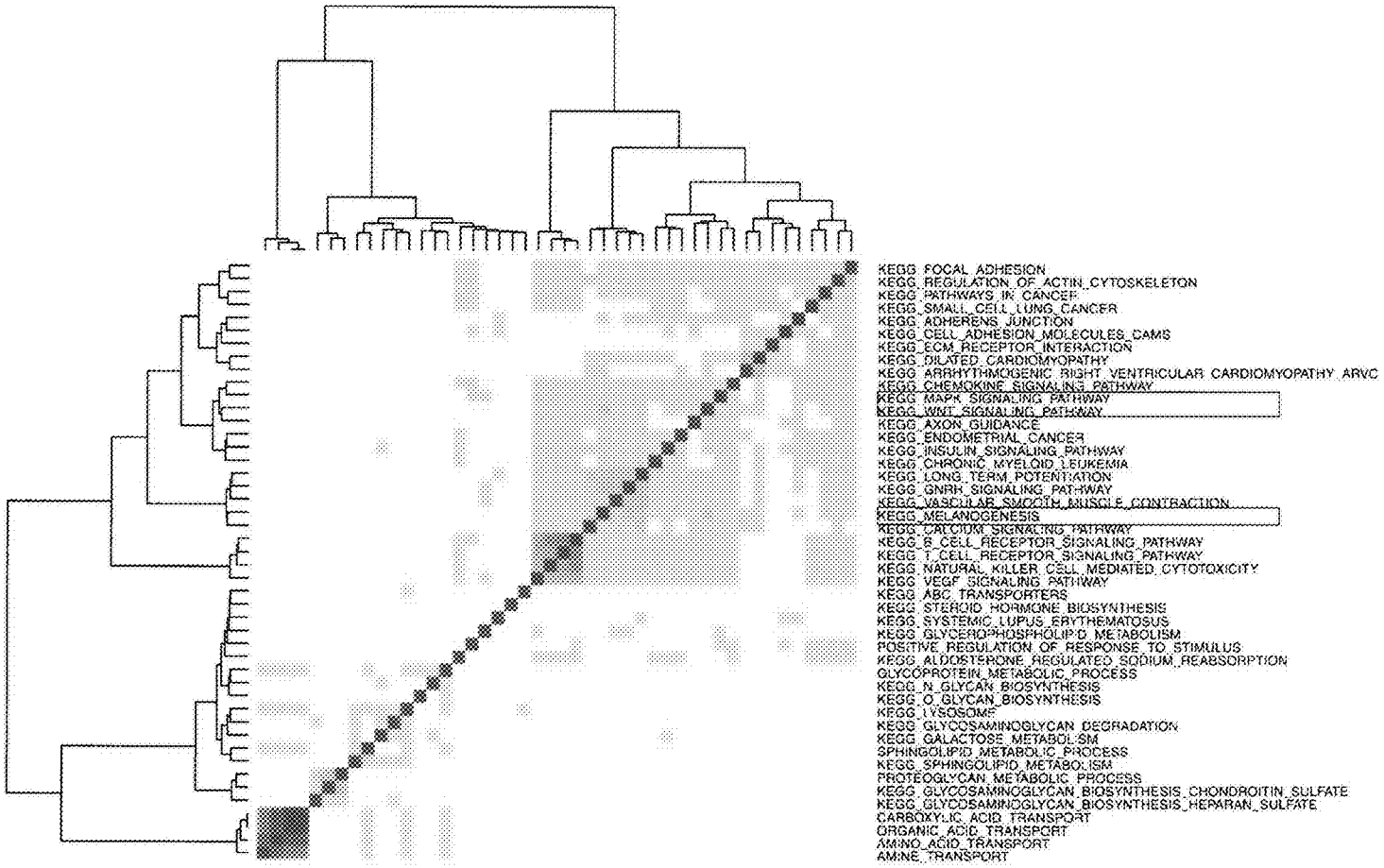

Importantly, knock-down of LINC01212 sensitizes BRAFV600E-melanoma cells to a BRAF-inhibitor currently used in the clinic, PLX3042 (FIG. 16). Without being bound to a particular mechanism, the fact that LINC01212 inhibition induces apoptosis of melanoma cells independent of B-raf, N-ras or p53 status, as well as results in inhibition of all known survival pathways (see Example 4), indicates that this synergistic effect will be observed for other chemotherapeutics as well (particularly those therapeutics that interact with those targets or are sensitive to resistance using the survival pathways). Preliminary data confirm this, and experiments on synergistic effects with combinations with MEK inhibitors, cisplatin and melphalan are currently ongoing.

Example 4

Pathway and Interaction Analysis

A full-genome transcriptome gene expression analysis was performed in these short-term melanoma culture cells in order to identify pathways that could account for the observed biological effect (induction of apoptosis). Remarkably, all known melanoma survival pathways are inactivated upon knock-down of the LINC01212-encoded lncRNA: WNT:Bcat, MAPK (through down-regulation of both MEK1 and MEK2) and MITF (FIGS. 17A-19B). As melanoma is known to be particularly refractory to cancer therapy, this concomitant inactivation of all survival pathways offers high therapeutic potential. In addition, it appears that a p53/P63 pro-apoptotic signature is induced (even in cells harboring TP53 inactivation mutations).

Ongoing experiments aimed at identifying the total/nuclear/cytoplasmic 525 interactomes should shed light on the molecular mechanisms underlying 525 melanoma protective function. Identification of polypeptides interacting with the endogenously expressed LINC01212 transcript in SK-MEL28 cells by MS in ongoing.

Example 5

Expression of LINC01212 can be Detected in Serum

Figure 20:
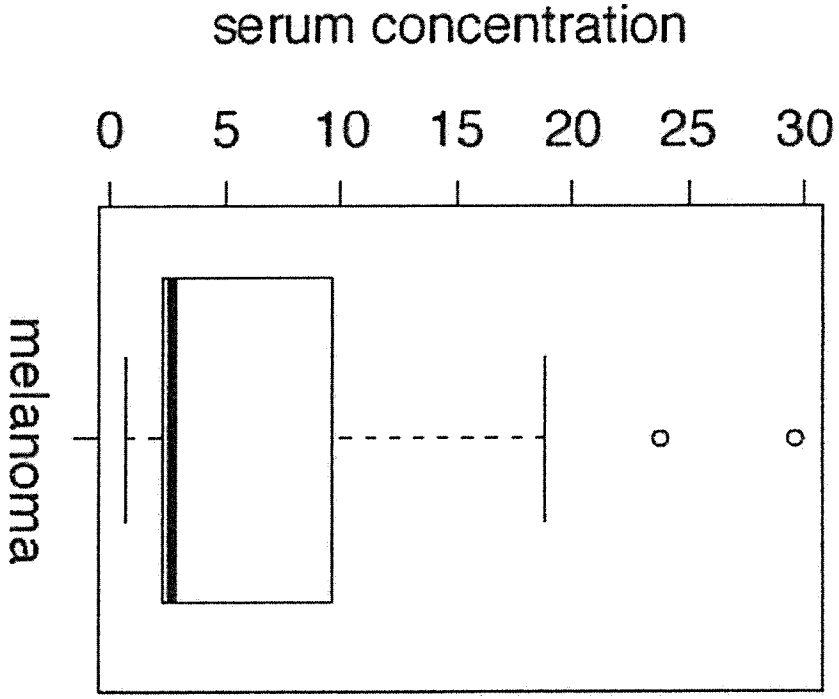
FIG. 20 illustrates detection of LINC01212 transcript in serum of melanoma patients. Units are cDNA copies per 2.5 μl serum.

Given the up-regulation very early during melanomagenesis, coinciding with the switch from benign (immortalized) to fully transformed melanoma (FIG. 6), the potential of LINC01212 as a melanoma biomarker was further explored. Particularly, it was evaluated whether LINC01212 could be detected in serum from melanoma patients, as blood or serum is easy to collect as a sample. As shown in FIG. 20, LINC01212 can be found in serum of melanoma patients. In contrast, the LINC01212 transcript cannot be detected in the serum of healthy volunteers.

Conclusions

Given its melanoma-specific expression profile, these data indicate that therapeutics that target this lncRNA could serve as melanoma-specific MAPK inhibitors, irrespective of how MAPK signaling is activated.

- LINC01212 is a melanoma-specific lncRNA that could serve as an early diagnostic marker of malignant transformation.
- LINC01212 could actively contribute to melanomagenesis in a previously unrecognized manner, particularly in samples with MITF co-amplification.
- LINC01212 is a key therapeutic target in melanoma.
- LINC01212 inhibition is a good candidate for combination therapy with other chemotherapeutics, such as BRAF-inhibitors.

Further development includes additional validation of the phenotype in vitro, including cell lines with differential KRAS and BRAF status and in vivo using xenografts and melanoma mouse models. Also, phenotypic and molecular characterization of primary melanocytes with LINC01212 overexpression and further molecular characterization of melanoma cell lines with LINC01212 overexpression or knock-down will be performed. Further validation of LINC01212 transcript as a serum marker for melanoma is currently ongoing, by testing in a larger patient population. Experiments aimed at elucidating the underlying mechanism by which down-regulation of this lncRNA induces apoptosis will also be performed.

SEQUENCE LISTING

```
<160> NUMBER OF SEQ ID NOS: 3

<210> SEQ ID NO 1
<211> LENGTH: 2044
<212> TYPE: DNA
<213> ORGANISM: Homo sapiens

<400> SEQUENCE: 1

ctgaagtcgc tagacatttg aggaacacat ccggggaaga agacacaggt ggctggtcat      60

ggagagcccg ctgggggaag agcacacaga caggcaccgg caggccattg accagcggga     120

caaggtgggc tcaatgtcat cacaagggtg cttaagaggg aaagaggaag ccatgagggt     180

cagagtcaaa ggaagacttg aagatactac actgcggact ttaaagatga aggaaggggc     240

gaaaaccaag aatgtgggaa gcctctagaa gctagagaag gcaaggaaac aaattttcca     300

ctagagcctc cagaaggaac acagccctgc tgacccactg taatgtctga cctctagatg     360

tgtaagggta gtaagactga aagtctcaga aaggcactgt taaattctta ttcctcaact     420

atgcaactca aaactggggt cctcagcagt gagcgagggg tgagagaaga cactgtataa     480

acatggcaca tcctcctgga aagtcaactt tactcaaagc tttagaaacc cagctcaaac     540
```

```
tagctgaagc agaaaagaca ttactgcgcc tataagttga aactttggag ggataaattt    600
cagaggtgtg gctagatcca acggctctct ggaaaactct gtgaaaaaaa tgcttcctca    660
agtccagaaa ccagaagctc aggaaattgt tgcttggttc ctcttgttag aggcagagat    720
tattcaacga cctacagggt agcgtttgaa cattgttacc aggaatcttt actttgccat    780
cttccaagtc tgttctcctc agtattggtt tcatttacaa gcaggccatc tctgccctca    840
tggcaatgat ggtctttact ccaggcttaa gacccttact atctactatt tccaaagcgg    900
agagagaact tcccacacct agtgacctgt gacacaggat tttatccttc gtacagaggg    960
aattcagttg gctaacataa tctgccttcc aatggagtaa gaatgtctgg actctttcct   1020
tcacctaccc ccaagacatg gaggcgtcta aaagataaat aaaacttggc aactgaccga   1080
aggaggaaga ggggatttca ggcaaaatca acgctgttca ctacgaggag acttcagaaa   1140
ggttgcctgc ttctggggag catagtccct gattcctcaa gacatacgtt tattcttttc   1200
ttcaatgtct ttgcctgcag tcaaaacaaa accattacct ttagccaagt tcacacattt   1260
cagccaaatc catatgcatc ggatcagttc tgtaggttat gggtgagcat gaacatataa   1320
aagaggcacc tgcctgtgcc tatctactcc atggaatttc aaaaggggcc acttatggag   1380
aatgtcttta gggacagaac caaccaccct gtctttcctc caactctcaa agtaacttct   1440
ggctttaatc ctcaagtgtc tatgctggag tttaagaaaa atgtttttca tagaattcat   1500
gtgtatgata ttgcatgagt tgtccatctt tgtatatatc tcaagacttg tggtgttagt   1560
taaagattca gagctctgtg tcctgaacac agagtaatac cagcattact aaggatgatc   1620
gtgggatttt aaaattcctc ccttagatag atcttacgaa cttatgttac caatcaacat   1680
aagttaagac aaaaagagca aatttagatg taaaaccatc ttggggccag gtgctgtggc   1740
tcacgcctgt aatcccagca ctttgggagg ccgaggcggg cggatcacta ggtcaggaga   1800
tcgagaccat cttggccaac acggtgaaac cctgtctcta ctaaaaatac aaaaaaatta   1860
gccgggcatg gtggcaggcg cctgtagtcc cagctactag ggaggctgag gcaggagaat   1920
ggtgtgaacc ctggaagcgg agcttgcagt gagccaagat catgccactg cactgcagct   1980
tgggcgacag agcgagactc cgtctcaaaa aaaaccaaac caacaaacaa acaaacaaaa   2040
aaaa                                                                2044
```

<210> SEQ ID NO 2
<211> LENGTH: 513
<212> TYPE: DNA
<213> ORGANISM: Homo sapiens

<400> SEQUENCE: 2

```
gaggaaggcg ggtccctggc tcggctctac ccccatggat ctaggtgggc tcaatgtcat     60
cacaagggtg cttaagaggg aaagaggaag ccatgagggt cagagtcaaa ggaagacttg    120
aagatactac actgcggact ttaaagatga aggaaggggc gaaaaccaag aatgtgggaa    180
gcctctagaa gctagagaag gcaaggaaac aaattttcca ctagagcctc cagaaggaac    240
acagccctgc tgacccactg taatgtctga cctctagatg tgtaagggta gtaagactga    300
aagtctcaga aaggcactgt taaattctta ttcctcaact atgcaactca aaactggggt    360
cctcagcagt gagcgagggg tgagagaaga cactgtataa acatggcaca tcctcctgga    420
aagtcaactt tactcaaagc tttagaaacc cagctcaaac tagctgaagc agaaaagaca    480
ttactgcgcc tataagttga aactttggag gga                                 513
```

<210> SEQ ID NO 3
<211> LENGTH: 4063
<212> TYPE: DNA
<213> ORGANISM: Homo sapiens

<400> SEQUENCE: 3 ctgaagtcgc tagacatttg aggaacacat ccggggaaga agacacaggt ggctggtcat 60 ggagagcccg ctgggggaag agcacacaga caggcaccgg caggccattg accagcggga 120 caaggtgggc tcaatgtcat cacaagggtg cttaagaggg aaagaggaag ccatgagggt 180 cagagtcaaa ggaagacttg aagatactac actgcggact ttaaagatga aggaaggggc 240 gaaaaccaag aatgtgggaa gcctctagaa gctagagaag gcaaggaaac aaattttcca 300 ctagagcctc cagaaggaac acagccctgc tgacccactg taatgtctga cctctagatg 360 tgtaagggta gtaagactga aagtctcaga aaggcactgt taaattctta ttcctcaact 420 atgcaactca aaactggggt cctcagcagt gagcgagggg tgagagaaga cactgtataa 480 acatggcaca tcctcctgga aagtcaactt tactcaaagc tttagaaacc cagctcaaac 540 tagctgaagc agaaaagaca ttactgcgcc tataagttga aactttggag ggataaattt 600 cagaggtgtg gctagatcca acggctctct ggaaaactct gtgaaaaaaa tgcttcctca 660 agtccagaaa ccagaagctc aggaaattgt tgcttggttc ctcttgttag aggcagagat 720 tattcaacga cctacagggt agcgtttgaa cattgttacc aggaatcttt actttgccat 780 cttccaagtc tgttctcctc agtattggtt tcatttacaa gcaggccatc tctgccctca 840 tggcaatgat ggtctttact ccaggcttaa gacccttact atctactatt tccaaagcgg 900 agagagaact tcccacacct agtgacctgt gacacaggat tttatccttc gtacagaggg 960 aattcagttg gctaacataa tctgccttcc aatggagtaa gaatgtctgg actctttcct 1020 tcacctaccc ccaagacatg gaggcgtcta aaagataaat aaaacttggc aactgaccga 1080 aggaggaaga ggggatttca ggcaaaatca acgctgttca ctacgaggag acttcagaaa 1140 ggttgcctgc ttctggggag catagtccct gattcctcaa gacatacgtt tattcttttc 1200 ttcaatgtct ttgcctgcag tcaaaacaaa accattacct ttagccaagt tcacacattt 1260 cagccaaatc catatgcatc ggatcagttc tgtaggttat gggtgagcat gaacatataa 1320 aagaggcacc tgcctgtgcc tatctactcc atggaatttc aaaaggggcc acttatggag 1380 aatgtcttta gggacagaac caaccaccct gtctttcctc caactctcaa agtaacttct 1440 ggctttaatc ctcaagtgtc tatgctggag tttaagaaaa atgtttttca tagaattcat 1500 gtgtatgata ttgcatgagt tgtccatctt tgtatatatc tcaagacttg tggtgttagt 1560 taaagattca gagctctgtg tcctgaacac agagtaatac cagcattact aaggatgatc 1620 gtgggatttt aaaattcctc ccttagatag atcttacgaa cttatgttac caatcaacat 1680 aagttaagac aaaaagagca aatttagatg taaaaccatc ttggggccag gtgctgtggc 1740 tcacgcctgt aatcccagca ctttgggagg ccgaggcggg cggatcacta ggtcaggaga 1800 tcgagaccat cttggccaac acggtgaaac cctgtctcta ctaaaaatac aaaaaaatta 1860 gccgggcatg gtggcaggcg cctgtagtcc cagctactag ggaggctgag gcaggagaat 1920 ggtgtgaacc ctggaagcgg agcttgcagt gagccaagat catgccactg cactgcagct 1980 tgggcgacag agcgagactc cgtctcaaaa aaaaccaaac caacaaacaa acaaacaaaa 2040 aaaagcacat tgaaaatgac atgatctatc ccaaggaata gcttaagacc tgatccactt 2100 aaacagctcc aagtgattta tcataaatgt gcttatttgg aaggtttagc agtaaccgct 2160

-continued

```
tatgggaggt ggtggggtta actaccaaaa ttgtacataa cttggatcct gtgtatggca   2220
attaatcaag aaattatatt ctttgacttt ctaacaaccc acacagagtg ctacatctgt   2280
ggcatgttta aagagagagc gagggatgaa atatttcttc taataaaatg ctaatggctt   2340
tgttttggag aaaaaatatt ggattattgt ggtgttagat ttatctgtat gaggatttct   2400
cgagtcacag tcagtaagta cttctgacag aaaaccagct atgtcctgaa tacaatatcc   2460
cagtcttcta aatgacttca ggattatgga gaggcccctt tataatactg aagaaagaac   2520
acaggaataa atggtgtgat agagaactgt agcagtcgaa gttattactg tgagcatttg   2580
ttaaatgttc aagagtattt atttaaccca aagcacattg gaatatgtta attaagacag   2640
gtgaggcatc ccattgattt gtggtgtctc atgggcataa cttgcaccca cttagttgct   2700
ctagtcctta ggttttcaag attttgcggg gatgcctact gtggttagga acccagagct   2760
cactccttgg agggttagtt tcacaaattc aatatctgaa aacctaaaag taccatcatc   2820
taaaaagaaa aatttggggc aacaaaagcg ccaaagtata atgtcatttt cattcctatg   2880
atcctttgtg atgtggttca aatggcttat tttaatattt cacttttcaa tcagtagctt   2940
tttaaaaatg acaatttcac aaatgcttat ggagcatcta ctttgtgcct acactggcca   3000
agagacagaa agatggaata atacctgact tctacctttt aagatctcat agtgcagcaa   3060
aacagagagc tgtagcaaat atttgtaatg tgaaaagagc aacactcatg aaacagtcca   3120
gtgctggaca cttactgtag tagagacact gcatcaatga ttctctttta caggcaaggg   3180
aactgaagct tgtagagagg ttagatcaca cagttaacaa gaagagggac aagcatttac   3240
cggaagccct gtgtggttct ggatactcac atagtgcttg ccagacgccc ggcattgtgt   3300
ttagggcttt acactcatga cctcactcgg tcctcatgac aaccctatgc aggggatact   3360
ataattatcc ccatttcaca gatgagcaaa ctgagctctg agaaggagca acttgaccaa   3420
ggtcatgtag gtaatgtcag agcagcaatt tgaatatagg ctcttgacaa ctaaacttta   3480
ctgctgtgag atgtagaggc atttctgcct ggagctgcgg gaaggtacag agattagggc   3540
aaataaatta taagaagatt agaaatatgg tcttgataag gactttgaag ataatgctta   3600
tatcagactt ccttctgatc tgagtcaatt gaaggatgta tttttgaacc tttcagaaat   3660
ctctctataa gttatagatc tgaattttag tgagaatcta ttccattcct cggagtgcga   3720
aaatccaaca caatgtctgg gaattcagac ttataaaaat catacagaag taattcttaa   3780
aaaatctttt attttgaagt aattgtaggc tcataagagg ttgtaaaaat aagagagtta   3840
tagtatgccc ttcacccagc ttcctccaaa gttaacgttt tatataacca tagtacatat   3900
caaaagtggg aaatagactt tgacaaaata ctattcatta gaccacagat catatgggga   3960
tttcattagt ttttagatgc actctattgt tttgtatagt tcttttccat tttatcacct   4020
gtatagattt gtgtaaccac caagaagtaa tttgttttaa gct                     4063
```

The invention claimed is:

1. An inhibitor of functional expression of LINC01212, which inhibitor is selected from the group consisting of a gapmer and a synthetic siRNA, which inhibitor specifically binds to LINC01212 RNA and inhibits the [translation] *functional expression* of LINC01212.

2. The inhibitor according to claim 1, which selectively induces apoptosis in a melanoma cell.

3. The inhibitor according, to claim 2, which induces apoptosis in a melanoma cell independent of TP53, BRAF, NRAS or MEK status.

4. A medicament comprising:

an amount of the inhibitor of functional expression of LINC01212 of claim 1 effective to inhibit the [translation] *functional expression* of LINC01212 in a subject.

5. A method of treating a subject diagnosed as having melanoma, the method comprising:

administering to the subject [the] *an* inhibitor of functional expression of LINC01212 [of claim 1] so as to treat the subject, *wherein the inhibitor comprises an antisense oligonucleotide complementary to at least a*

*unique portion of the LINC01212 RNA, a siRNA targeting the LINC01212 RNA, or a shRNA targeting the LINC01212 RNA.*

6. A method of treating melanoma in a subject in need thereof, the method comprising:

administering an inhibitor of functional expression of LINC01212 to the subject, wherein the inhibitor is selected from the group consisting of a gapmer and a [synthetic] siRNA, which inhibitor specifically binds to LINC01212 RNA and inhibits the translation of LINC01212.

7. The method according to claim 6, further comprising:

administering an additional chemotherapeutic agent to the subject.

8. The method according to claim 7, wherein the additional chemotherapeutic agent is a Raf kinase inhibitor.

9. The method according to claim 8, wherein the Raf kinase inhibitor is a B-raf kinase inhibitor.

10. A method of treating a subject diagnosed as having melanoma, the method comprising:

inhibiting the [translation] *functional expression* of LINC01212 in the subject by administering to the subject a compound selected from the group consisting of [a gapmer, a synthetic siRNA, and any combination thereof] *an antisense oligonucleotide complementary to at least a unique portion of the LINC10121 RNA, a siRNA targeting the LINC01212 RNA and a shRNA targeting the LINC01212 RNA*, wherein the compound specifically binds to LINC01212 RNA and inhibits the [translation] *functional expression* of LINC01212, so as to induce apoptosis in a melanoma cell.

11. The method according to claim 10, wherein apoptosis independent of TP53, BRAF, NRAS or MEK status is induced in the subject.

*12. The method according to claim 5, wherein the antisense oligonucleotide comprises a locked nucleic acid, a peptide nucleic acid, or a morpholino.*

*13. The method according to claim 5, wherein the antisense oligonucleotide is a gapmer.*

*14. The method according to claim 10, wherein the antisense oligonucleotide comprises a locked nucleic acid, a peptide nucleic acid, or a morpholino.*

*15. The method according to claim 10, wherein the antisense oligonucleotide is a gapmer.*

* * * * *